US011083402B2

(12) United States Patent
Nelson et al.

(10) Patent No.: US 11,083,402 B2
(45) Date of Patent: Aug. 10, 2021

(54) PATIENT STATE DETERMINATION BASED ON ONE OR MORE SPECTRAL CHARACTERISTICS OF A BIOELECTRICAL BRAIN SIGNAL

(71) Applicant: Medtronic, Inc., Minneapolis, MN (US)

(72) Inventors: Dwight E. Nelson, Shoreview, MN (US); Jianping Wu, Shoreview, MN (US); Rahul Gupta, St. Louis Park, MN (US); Yan Zhao, Enschede (NL)

(73) Assignee: Medtronic, Inc., Minneapolis, MN (US)

( * ) Notice: Subject to any disclaimer, the term of this patent is extended or adjusted under 35 U.S.C. 154(b) by 678 days.

(21) Appl. No.: 13/955,367

(22) Filed: Jul. 31, 2013

(65) Prior Publication Data
US 2014/0358024 A1 Dec. 4, 2014

Related U.S. Application Data

(60) Provisional application No. 61/831,014, filed on Jun. 4, 2013.

(51) Int. Cl.
*A61B 5/00* (2006.01)
*A61B 5/374* (2021.01)
*A61B 5/316* (2021.01)
*A61N 1/36* (2006.01)

(52) U.S. Cl.
CPC .............. *A61B 5/316* (2021.01); *A61B 5/374* (2021.01); *A61B 5/4833* (2013.01);
(Continued)

(58) Field of Classification Search
None
See application file for complete search history.

(56) References Cited

U.S. PATENT DOCUMENTS 5,601,090 A * 2/1997 Musha ................. A61B 5/0482
128/925
7,385,443 B1 6/2008 Denison
(Continued)

FOREIGN PATENT DOCUMENTS

CN 1381219 11/2002
CN 1325014 C 7/2007
(Continued)

OTHER PUBLICATIONS

International Search Report and Written Opinion from counterpart International Application No. PCT/US2014/033462, dated Jul. 14, 2014, 8 pp.
(Continued)

*Primary Examiner* — Etsub D Berhanu
(74) *Attorney, Agent, or Firm* — Shumaker & Sieffert, P.A.

(57) ABSTRACT

In some examples, a processor determines a patient state based on activity of a bioelectrical brain signal of a patient in one or more frequency sub-bands of a frequency band of interest. For example, a processor may determine a patient state based on the power level of a bioelectrical brain signal of the patient in one or more frequency sub-bands of a frequency band, or based on a spectral pattern of a bioelectrical brain signal in a frequency band, such as a shift in a power distribution between sub-bands, a change in the peak frequency within one or more sub-bands, a pattern of the power distribution over one or more frequency sub-bands, or a width or a variability of one or more sub-bands exhibiting a relatively high or low level of activity.

42 Claims, 11 Drawing Sheets

(52) U.S. Cl.
CPC ........ *A61B 5/7282* (2013.01); *A61N 1/36139* (2013.01); *A61B 5/4064* (2013.01)

(56) References Cited

U.S. PATENT DOCUMENTS

| | | | |
|---|---|---|---|
| 8,000,796 B2 | 8/2011 | Tass et al. | |
| 8,280,514 B2 | 10/2012 | Lozano et al. | |
| 8,290,596 B2 | 10/2012 | Wei et al. | |
| 8,380,314 B2 | 2/2013 | Panken et al. | |
| 2001/0029391 A1* | 10/2001 | Gluckman | A61N 1/36014 607/2 |
| 2002/0082511 A1* | 6/2002 | Carlebach | A61B 5/0836 600/529 |
| 2002/0148477 A1* | 10/2002 | Kwoen | A61B 5/0002 340/573.1 |
| 2005/0208969 A1 | 9/2005 | Kwoen | |
| 2007/0197930 A1* | 8/2007 | Sarkela | A61B 5/048 600/544 |
| 2008/0228100 A1* | 9/2008 | Navakatikyan | A61B 5/0476 600/544 |
| 2009/0082691 A1 | 3/2009 | Denison et al. | |
| 2009/0099627 A1 | 4/2009 | Molnar et al. | |
| 2009/0247894 A1* | 10/2009 | Causevic | A61B 5/0478 600/544 |
| 2011/0144521 A1 | 6/2011 | Molnar et al. | |
| 2013/0267866 A1* | 10/2013 | Nakashima | A61B 5/048 600/544 |

FOREIGN PATENT DOCUMENTS

| | | |
|---|---|---|
| CN | 101848677 A1 | 9/2010 |
| WO | 2009051638 A1 | 4/2009 |
| WO | 2013012739 A1 | 1/2013 |

OTHER PUBLICATIONS

Third Office Action and translation thereof, from counterpart Chinese Application No. 201480044057, dated Dec. 26, 2018, 28 pp.
Fourth Office Action and translation thereof, from counterpart Chinese Application No. 201480044057, dated Apr. 1, 2019, 22 pp.
Examination Report from counterpart European Application No. 14722393.7, dated Oct. 11, 2018, 4 pp.
Response to Examination Report dated Oct. 11, 2018, from counterpart European Application No. 14722939.7, filed Feb. 21, 2019, 8 pp.
Notice Intent to Grant and Text Intended to Grant from counterpart European Application No. 14722393.7, dated Nov. 21, 2019, 71 pp.
International Preliminary Report on Patentability from International Application No. PCT/US2014/033462, dated Dec. 8, 2015, 4 pp.
Response to Communication under Rules 161(1) and 162 EPC, filed Aug. 18, 2016 from counterpart European Application No. 14722939.7, 5 pp.
Preliminary Amendment from counterpart European Application No. 14722939.7, filed Jan. 4, 2016, 19 pp.
Communication Pursuant to Rules 161(1) and 162 EPC dated Feb. 9, 2016 from counterpart European Application No. 14722939.7, 2 pp.
First Office Action and Search Report, and translation thereof, from counterpart Chinese Application No. 201480044057.X, dated Dec. 4, 2017, 24 pp.
Second Office Action and Search Report, and translation thereof, from counterpart Chinese Application No. 201480044057.X, dated Jul. 5, 2018, 11 pp.
First Office Action and Search Report, and translation thereof, from counterpart Chinese Application No. 202010807206.0, dated Mar. 31, 2021, 18 pp.

\* cited by examiner

PATIENT STATE DETERMINATION BASED ON ONE OR MORE SPECTRAL CHARACTERISTICS OF A BIOELECTRICAL BRAIN SIGNAL

This application claims the benefit of U.S. Provisional Application No. 61/831,014, filed on Jun. 4, 2013 and entitled "PATIENT STATE DETERMINATION BASED ON ONE OR MORE SPECTRAL CHARACTERISTICS OF A BIOELECTRICAL BRAIN SIGNAL," the entire content of which is incorporated herein by reference.

TECHNICAL FIELD

The disclosure relates to patient monitoring with a medical device.

BACKGROUND

Medical devices, such as electrical stimulators or therapeutic agent delivery devices, may be used in different therapeutic applications, such as deep brain stimulation (DBS), spinal cord stimulation (SCS), pelvic stimulation, gastric stimulation, peripheral nerve stimulation, functional electrical stimulation or delivery of pharmaceutical agent, insulin, pain relieving agent or anti-inflammatory agent to a target tissue site within a patient. A medical device may be configured to deliver therapy to a patient to treat a variety of symptoms or patient conditions such as chronic pain, tremor, Parkinson's disease, other types of movement disorders, seizure disorders (e.g., epilepsy), urinary or fecal incontinence, sexual dysfunction, obesity, mood disorders, gastroparesis or diabetes. In some therapy systems, an electrical stimulator, which may be implantable in some instances, delivers electrical therapy to a target tissue site within a patient with the aid of one or more electrodes, which may be deployed by medical leads, on a housing of the electrical stimulator, or both. In addition to or instead of electrical stimulation therapy, a medical device, which may be implantable in some instances, may deliver a therapeutic agent to a target tissue site within a patient with the aid of one or more fluid delivery elements, such as a catheter or a therapeutic agent eluting patch.

Some medical devices are configured to sense a patient parameter, such as a bioelectrical brain signal. A sensed patient parameter may be used for various purposes, such as to control therapy delivery by a medical device.

SUMMARY

The disclosure describes example systems, devices, and methods for determining a patient state based on activity of a bioelectrical brain signal of a patient in one or more frequency sub-bands of a frequency band of interest. The activity of a bioelectrical brain signal in a particular frequency sub-band may be indicated by, for example, the signal strength (also referred to herein as "power," "power level," or "spectral amplitude") in the frequency sub-band. In some examples described herein, a patient state is determined based on the power level of a bioelectrical brain signal of the patient in one or more frequency sub-bands of a frequency band. The patient state can be, for example, a patient disease state, a state in which a symptom of a patient condition is observed, or a patient state indicative of the efficacy of therapy delivered by a medical device or the efficacy of medication.

In addition, or instead, in some examples, a patient state is determined based on a spectral pattern of a bioelectrical brain signal in the frequency band of interest, such as a shift in a power distribution between sub-bands of the frequency band (e.g., a change over time of the frequency sub-band in which a peak power level of the bioelectrical brain signal or a peak power within a frequency band of interest is observed), a change in the peak power level within one or more frequency sub-bands, a pattern of the power distribution of a sensed bioelectrical brain signal over one or more frequency sub-bands (e.g., whether a plot of the power level versus frequency illustrates a narrow peak, a broad peak, a unimodal peak, or a bimodal peak), or a width or a variability (e.g., in the width) of one or more frequency sub-bands exhibiting a relatively high or low level of activity.

Different frequency bands of a bioelectrical brain signal may be associated with different brain activity of the patient. The brain activity may be, for example, associated with a patient-initiated state (e.g., e.g., a movement state, a speech state, or a sleep state), a patient condition (e.g., a disease state), or the occurrence of a specific symptom of a patient condition. Example frequency bands include the delta band, alpha band, beta band, gamma band, and high gamma band. A frequency band may include a plurality of frequency sub-bands, which each have a width that is narrower than the frequency band. The frequency band may be defined by a plurality of frequency sub-bands. Brain activity within one or more particular frequency sub-bands, as opposed to activity in the broader frequency band itself, may be indicative of particular patient states. The activity within a frequency sub-band can be indicated by a power level (or amplitude) within the frequency sub-band.

In some examples, a processor determines a patient state based on activity of a bioelectrical brain signal of a patient in one or more frequency sub-bands of a frequency band of interest and generates an indication of the determined patient state. The processor may control therapy delivery to the patient based on the determined patient state, monitor a patient condition based on the determined patient state, generate a patient diagnosis (e.g., determines a patient condition sub-type) based on the determined patient state, or any combination thereof.

In some examples, the disclosure describes example systems, devices, and methods for determining whether a patient has Parkinson's disease or another patient condition based on activity of a bioelectrical brain signal of a patient in one or more frequency sub-bands of a frequency band of interest. In some cases, bioelectrical brain signals of patients without Parkinson's disease may not exhibit certain activity in one or more frequency sub-bands of a frequency band of interest, whereas bioelectrical brain signals of patients with Parkinson's disease may exhibit certain activity in one or more frequency sub-bands of a frequency band of interest. Thus, this activity in one or more frequency sub-bands of a frequency band of interest may be indicative of the presence of Parkinson's disease and may, therefore, be used in some examples to diagnose Parkinson's disease.

In one example, the disclosure is directed to a method that comprises receiving, with one or more processors, information representative of a bioelectrical brain signal of a patient, determining, with the one or more processors, a patient state based on activity of the bioelectrical brain signal within one or more frequency sub-bands of a frequency band of the bioelectrical brain signal, and generating, with the one or more processors, an indication of the determined patient state.

In another example, the disclosure is directed to a system that comprises a sensing module configured to sense a bioelectrical brain signal of a patient, and one or more processors configured to determine a patient state based on activity of the bioelectrical brain signal within one or more frequency sub-bands of a frequency band of the bioelectrical brain signal, and generate an indication of the determined patient state.

In another example, the disclosure is directed to a system that comprises means for sensing a bioelectrical brain signal of a patient, and means for determining a patient state based on activity of the bioelectrical brain signal within one or more frequency sub-bands of a frequency band of the bioelectrical brain signal.

In another aspect, the disclosure is directed to a computer-readable medium containing instructions that, when executed by one or more processors, cause the one or more processors to receive information representative of a bioelectrical brain signal of a patient, and determine a patient state based on activity of the bioelectrical brain signal within one or more frequency sub-bands of a frequency band of the bioelectrical brain signal.

In one example, the disclosure is directed to a method that comprises receiving, with one or more processors, information representative of a bioelectrical brain signal of a patient, and determining, with the one or more processors, a biomarker indicative of a patient state, wherein determining the biomarker comprises determining a characteristic of the bioelectrical brain signal within one or more frequency sub-bands of a frequency band of the bioelectrical brain signal indicative of the patient state.

In another example, the disclosure is directed to a system that comprises a sensing module configured to sense a bioelectrical brain signal of a patient, and one or more processors configured to determine a biomarker indicative of a patient state by at least determining a characteristic of the bioelectrical brain signal within one or more frequency sub-bands of a frequency band of the bioelectrical brain signal indicative of the patient state.

In another example, the disclosure is directed to a system that comprises means for sensing a bioelectrical brain signal of a patient, and means for determining a biomarker indicative of a patient state, wherein the biomarker comprises a characteristic of the bioelectrical brain signal within one or more frequency sub-bands of a frequency band of the bioelectrical brain signal indicative of the patient state.

In another aspect, the disclosure is directed to a computer-readable medium containing instructions that, when executed by one or more processors, cause the one or more processors to receive information representative of a bioelectrical brain signal of a patient, and determine a biomarker indicative of a patient state, wherein the biomarker comprises a characteristic of the bioelectrical brain signal within one or more frequency sub-bands of a frequency band of the bioelectrical brain signal indicative of the patient state.

In another aspect, the disclosure is directed to a computer-readable storage medium, which may be an article of manufacture. The computer-readable storage medium includes computer-readable instructions for execution by one or more processors. The instructions cause one or more processors to perform any part of the techniques described herein. The instructions may be, for example, software instructions, such as those used to define a software or computer program.

The details of one or more examples are set forth in the accompanying drawings and the description below. Other features, objects, and advantages will be apparent from the description and drawings, and from the claims.

DETAILED DESCRIPTION

Figure 1:
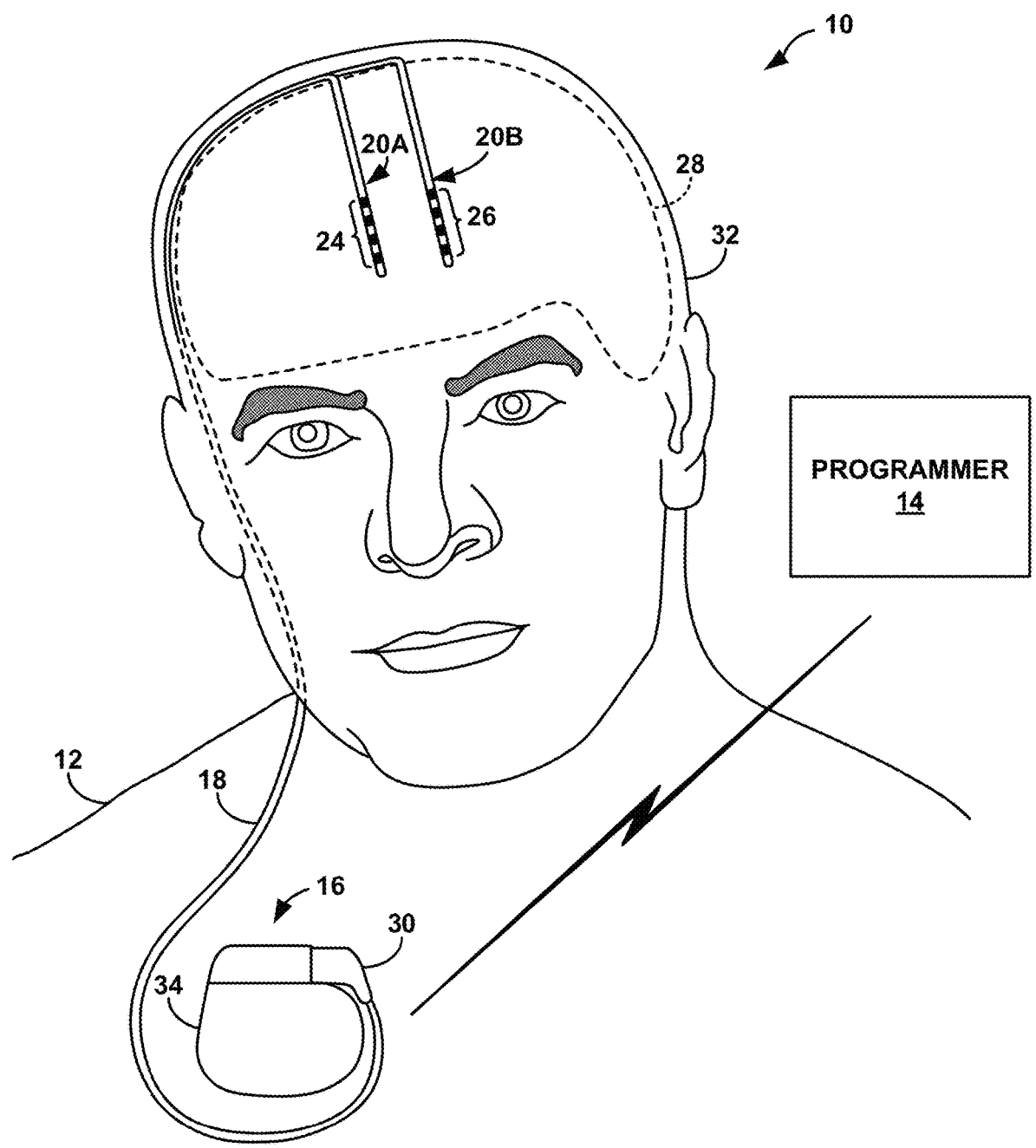
FIG. 1 is a conceptual diagram illustrating an example deep brain stimulation (DBS) system configured to sense a bioelectrical brain signal and deliver electrical stimulation therapy to a tissue site within a brain of a patient.

The disclosure describes example systems, devices, and methods for determining a patient state based on one or more frequency domain characteristics of a bioelectrical brain signal of a patient, and, in particular activity in one or more frequency sub-bands of a frequency band of interest. The activity of a bioelectrical brain signal in a particular frequency sub-band may be indicated by, for example, the signal strength (also referred to herein as "power," "power level," or "spectral amplitude") in the frequency sub-band. Thus, a peak power level within a frequency band may be, for example, the greatest signal strength in the frequency band. The peak power level of a sensed bioelectrical brain signal may also be referred to as an "oscillation peak" in some examples.

The activity of a bioelectrical brain signal of a patient in one or more frequency sub-bands of a frequency band of interest that may be indicative of a patient state includes, for example, a spectral pattern of a bioelectrical brain signal, a power level of a bioelectrical brain signal in one or more frequency sub-bands (e.g., two or more frequency sub-bands) of a frequency band, or both. The patient state can be, for example, a patient disease state, a state in which a symptom of a patient condition is observed, or a patient state indicative of the efficacy of therapy delivery by a medical device or the efficacy of medication.

Different frequency bands of a bioelectrical brain signal are associated with different brain activity of the patient. One example of the frequency bands is shown in Table 1 below:

TABLE 1

| Frequency (f) Band Hertz (Hz) | Frequency Information |
|---|---|
| f < 4 Hz | δ (delta frequency band) |
| 4 Hz ≤ f < 8 Hz | theta frequency band |
| 8 Hz ≤ f < 13 Hz | α (alpha frequency band) |
| 13 Hz < f < 35 Hz | β (beta frequency band) |
| 35 Hz ≤ f < 100 Hz | γ (gamma frequency band) |
| 100 Hz < f < 400 Hz | high γ (high gamma frequency band) |

In other examples, however, the frequency bands may have different frequency ranges. A frequency band may include (e.g., may be made up of) a plurality of frequency sub-bands, which each have a width that is narrower than the frequency band. The frequency sub-bands of a frequency band may have substantially the same (e.g., the same or nearly the same) widths or different widths.

The activity within a particular frequency band of a sensed bioelectrical brain signal may change as a function of one or more patient states. For example, the activity within a particular frequency band of a sensed bioelectrical brain signal may be indicative of a patient-initiated state (e.g., a movement state, a speech state, or a sleep state) or a patient state indicative of the occurrence of one or more patient symptoms associated with a patient condition. The patient state indicated by the activity within a particular frequency band may or may not be the result of volitional patient activity.

A frequency band, e.g., each of the frequency bands indicated above, includes a plurality of frequency sub-bands, which are each defined by a narrower frequency band than the frequency band. It is believed that the activity within one or more particular frequency sub-bands, as opposed to activity in the broader frequency band itself, may be better indicative of a specific patient state than the power level in the broader frequency band. These specific patient states may, for example, provide a better indication of the progression of a patient condition (e.g., the patient pathology), the therapeutic effect of a particular therapy (e.g., electrical stimulation therapy or pharmaceutical medications), the presence of a symptom of a patient condition, the presence or absence of a patient condition, or any combination thereof.

While the power level of the bioelectrical brain signal in a particular frequency band may be useful for determining a patient state (e.g., a movement state, a sleep state, a speech state, or a disease state), in some cases, a patient state determination based on the power level in one or more frequency sub-bands may provide a better specificity of the patient state and a better granularity of patient state determinations. For example, a movement state may be indicated by changes in not only the amplitude of beta band activity of a bioelectrical brain signal, but also changes in (e.g., increasing or decreasing shifts) in the peak frequency of beta band activity during movements. This can be indicated by, for example, the frequency sub-band of the beta band in which the peak power level within the overall beta band is observed.

The power level of the bioelectrical brain signal in one or more frequency sub-bands of a frequency band of interest may have a better correlation to specific patient states compared to the total power level in the frequency band of interest. In this way, the frequency components of activity in a frequency band of a bioelectrical brain signal may indicate a fuller picture of a patient condition than the power level of in the frequency band alone. The frequency components include, for example, the power level of the bioelectrical brain signal in one or more frequency sub-bands of the frequency band.

The more specific patient state determinations made based on the power level in one or more frequency sub-bands of a frequency band of interest may be useful for monitoring a patient condition (e.g., the progression of the patient disease state), generating a patient diagnosis (e.g., determining a presence or absence of a patient condition or determining a patient condition sub-type, such as a particular type of patient condition or a severity of a particular patient condition), controlling therapy delivery, or any combination thereof.

It is believed that one or more characteristics of the bioelectrical brain signal in the one or more frequency sub-bands of a frequency band of interest may be revealing of specific patient states. For example, it is believed that a spectral pattern of a bioelectrical brain signal may be revealing of specific patient states. The spectral pattern can be indicated by, for example, the distribution of the signal strength (e.g., as indicated by the power level) over one or more frequency sub-bands of a frequency band of interest or over a plurality of frequency bands of interest. Example spectral patterns that may be indicative of an occurrence of a particular patient state include, for example, a shift in a power distribution between sub-bands of the frequency band over time (e.g., a change in the frequency sub-band in which a peak power level of the signal across all frequency bands or a peak power within a frequency band of interest is observed, or the ratio of power distributions between two or more frequency sub-bands), a change in the peak power level within one or more frequency sub-bands, a pattern of the power distribution over one or more frequency sub-bands (e.g., whether a plot of the power level versus frequency illustrates a narrow peak, a broad peak, a uni-modal peak, or a bimodal peak, the peak being the peak amplitude within the frequency band or frequency sub-band), a width or a variability (e.g., in the width) of one or more frequency sub-bands exhibiting a relatively high or low level of activity, or other characteristics observed in the distribution of the signal strength over one or more frequency sub-bands of a frequency band of interest or over a plurality of frequency bands of interest.

The pattern of the power distribution over one or more frequency sub-bands indicative of a particular patient state can be within the same frequency band or over one or more frequency bands. The spectral pattern, as well as other frequency domain characteristics of a bioelectrical brain signal, may be determined based on any suitable transform of the sensed bioelectrical brain signal, such as, but not limited to, a Fast Fourier Transform.

While short duration recordings (e.g., on the order of seconds) of a bioelectrical brain signal may indicate the power level within a particular frequency band of interest, the short duration recordings may not indicate spectral patterns of the bioelectrical brain signal. Thus, the short duration recordings may not provide a full picture of the progression of pathological activity of a patient. In contrast, relatively long term recordings (e.g., on the order of minutes, hours, or even days) of a bioelectrical brain signal may reveal spectral patterns or a change in the peak power level over time that offer a better picture of the progression of the pathological activity of the patient.

In some examples disclosed herein, a processor of a device (alone or in combination with another processor) determines a patient state based on activity of a bioelectrical brain signal of the patient in one or more frequency sub-bands of a frequency band. For example, the processor may determine a patient state based on the power level in one or more particular frequency sub-bands of a frequency band, based on the spectral patterns of a bioelectrical brain signal (e.g., a shift in dominant power from one frequency sub-band to another over time, a change in the frequency sub-band in which the peak power within the frequency band is observed, a shape of a plot indicating the distribution of the signal strength), or any combination thereof. In some examples, the processor generates an indication of the determined patient state, controls therapy delivery to the patient based on the determined patient state, monitors a patient condition based on the determined patient state, generates a patient diagnosis (e.g., determines a patient condition sub-type) based on the determined patient state, or any combination thereof.

During a learning phase, oscillation spectra of a bioelectrical brain signal sensed in a brain of a patient may be assessed to determine spectral characteristics of a bioelectrical brain signal that are associated with one or more different patient states. Example patient states include, but are not limited to, normal brain function, abnormal brain function, specific patient symptoms, a movement state, a sleep state, a speech state, or a state in which an activity (e.g., a symptom) that occurs as a result of a patient condition is observed. Example spectral characteristics include, for example, power levels in one or more frequency sub-bands, spectral patterns, or any combination thereof. These spectral characteristics may be, for example, stored by a device as biomarkers indicative of a particular patient state, such as normal or pathological behaviors, responses to medications or other therapies, including electrical therapies, or both.

As used herein, a "movement state" may include a state in which the patient is intending to move (e.g., initiating thoughts relating to moving a body part, e.g., a limb or a leg to initiate movement), is attempting to initiate movement or has successfully initiated movement and is currently moving. A "sleep state" may include a state in which the patient is intending on sleeping (e.g., initiating thoughts of sleep), is attempting to sleep or has initiated sleep and is currently sleeping. A "speech state" may include a state in which the patient is intending on speaking, is attempting to speak or has initiated speech.

FIG. 1 is a conceptual diagram illustrating an example therapy system 10 that is configured to deliver therapy to patient 12 to manage a disorder of patient 12. In some examples, therapy system 10 may deliver therapy to patient 12 to manage a movement disorder or a neurodegenerative impairment of patient 12. Patient 12 ordinarily will be a human patient. In some cases, however, therapy system 10 may be applied to other mammalian or non-mammalian non-human patients. A movement disorder may be characterized by one or more symptoms, such as, but not limited to, impaired muscle control, motion impairment or other movement problems, such as rigidity, bradykinesia, rhythmic hyperkinesia, nonrhythmic hyperkinesia, dystonia, tremor, and akinesia. In some cases, the movement disorder may be a symptom of Parkinson's disease or Huntington's disease. However, the movement disorder may be attributable to other patient conditions.

Although movement disorders are primarily referred to throughout the remainder of the application, in other examples, therapy system 10 may be configured to deliver therapy to manage other patient conditions, such as, but not limited to, seizure disorders (e.g., epilepsy), psychiatric disorders, behavior disorders, mood disorders, memory disorders, mentation disorders, Alzheimer's disease, or other neurological or psychiatric impairments, in addition to or instead of a movement disorder. Examples of psychiatric disorders include major depressive disorder (MDD), bipolar disorder, anxiety disorders, post traumatic stress disorder, dysthymic disorder, and obsessive compulsive disorder (OCD). Treatment of other patient disorders via delivery of therapy to brain 28 or another suitable target therapy delivery site in patient 12 is also contemplated.

In the example shown in FIG. 1, therapy system 10 includes medical device programmer 14, implantable medical device (IMD) 16, lead extension 18, and one or more leads 20A and 20B (collectively "leads 20") with respective sets of electrodes 24, 26. IMD 16 includes a therapy module that includes a stimulation generator that is configured to generate and deliver electrical stimulation therapy to one or more regions of brain 28 of patient 12 via a subset of electrodes 24, 26 of leads 20A and 20B, respectively. In the example shown in FIG. 1, therapy system 10 may be referred to as a deep brain stimulation (DBS) system because IMD 16 provides electrical stimulation therapy directly to tissue within brain 28, e.g., a tissue site under the dura mater of brain 28 or one or more branches or nodes, or a confluence of fiber tracks. In other examples, leads 20 may be positioned to deliver therapy to a surface of brain 28 (e.g., the cortical surface of brain 28). In some examples, IMD 16 may provide cortical stimulation therapy to patient 12, e.g., by delivering electrical stimulation to one or more tissue sites in the cortex of brain 28. In some examples, IMD 16 may provide vagal nerve stimulation (VNS) therapy to patient 12 by delivering electrical stimulation to one or more vagal nerve tissue sites.

Although electrical stimulation therapy is primarily referred to throughout the remainder of the application, in other examples, therapy system 10 may be configured to deliver other types of therapy in addition to or instead of electrical stimulation therapy, such as, e.g., drug delivery therapy.

In the example shown in FIG. 1, IMD 16 may be implanted within a subcutaneous pocket in the pectoral region of patient 12. In other examples, IMD 16 may be implanted within other regions of patient 12, such as a subcutaneous pocket in the abdomen or buttocks of patient 12 or proximate the cranium of patient 12. Implanted lead extension 18 is coupled to IMD 16 via connector block 30 (also referred to as a header), which may include, for example, electrical contacts that electrically couple to respective electrical contacts on lead extension 18. The electrical contacts electrically couple the electrodes 24, 26 carried by leads 20 to IMD 16. Lead extension 18 traverses from the implant site of IMD 16 within a chest cavity of patient 12, along the neck of patient 12 and through the cranium of patient 12 to access brain 28. IMD 16 can be constructed of a biocompatible material that resists corrosion and degradation from bodily fluids. IMD 16 may comprise a hermetic housing 34 to substantially enclose components, such as a processor, therapy module, and memory.

In the example shown in FIG. 1, leads 20 are implanted within the right and left hemispheres, respectively, of brain 28 in order to deliver electrical stimulation to one or more regions of brain 28, which may be selected based on many factors, such as the type of patient condition for which therapy system 10 is implemented to manage. Other implant sites for leads 20 and IMD 16 are contemplated. For example, IMD 16 may be implanted on or within cranium 32 or leads 20 may be implanted within the same hemisphere at multiple target tissue sites or IMD 16 may be coupled to a single lead that is implanted in one or both hemispheres of brain 28.

Leads 20 may be positioned to deliver electrical stimulation to one or more target tissue sites within brain 28 to manage patient symptoms associated with a disorder of patient 12. Leads 20 may be implanted to position electrodes 24, 26 at desired locations of brain 28 through respective holes in cranium 32. Leads 20 may be placed at any location within brain 28 such that electrodes 24, 26 are capable of providing electrical stimulation to target tissue sites within brain 28 during treatment. Different neurological or psychiatric disorders may be associated with activity in one or more of regions of brain 28, which may differ between patients. For example, a suitable target therapy delivery site within brain 28 for controlling a movement disorder of patient 12 may include one or more of the pedunculopontine nucleus (PPN), thalamus, basal ganglia structures (e.g., globus pallidus, substantia nigra or subthalamic nucleus), zona inserta, fiber tracts, lenticular fasciculus (and branches thereof), ansa lenticularis, and/or the Field of Forel (thalamic fasciculus). The PPN may also be referred to as the pedunculopontine tegmental nucleus.

As another example, in the case of MDD, bipolar disorder, OCD, or other anxiety disorders, leads 20 may be implanted to deliver electrical stimulation to the anterior limb of the internal capsule of brain 28, and only the ventral portion of the anterior limb of the internal capsule (also referred to as a VC/VS), the subgenual component of the cingulate cortex (which may be referred to as CG25), anterior cingulate cortex Brodmann areas 32 and 24, various parts of the prefrontal cortex, including the dorsal lateral and medial pre-frontal cortex (PFC) (e.g., Brodmann area 9), ventromedial prefrontal cortex (e.g., Brodmann area 10), the lateral and medial orbitofrontal cortex (e.g., Brodmann area 11), the medial or nucleus accumbens, thalamus, intralaminar thalamic nuclei, amygdala, hippocampus, the lateral hypothalamus, the Locus ceruleus, the dorsal raphe nucleus, ventral tegmentum, the substantia nigra, subthalamic nucleus, the inferior thalamic peduncle, the dorsal medial nucleus of the thalamus, the habenula, the bed nucleus of the stria terminalis, or any combination thereof. Target tissue sites not located in brain 28 of patient 12 are also contemplated.

As another example, in the case of a seizure disorder or Alzheimer's disease, for example, leads 20 may be implanted to deliver electrical stimulation to regions within the Circuit of Papez, such as, e.g., the anterior thalamic nucleus, the internal capsule, the cingulate, the fornix, the mammillary bodies, the mammillothalamic tract (mammillothalamic fasciculus), and/or hippocampus. For example, in the case of a seizure disorder, IMD 16 may deliver therapy to a region of brain 28 via a selected subset of electrodes 24, 26 to suppress cortical activity within the anterior thalamic nucleus, hippocampus, or other brain region associated with the occurrence of seizures (e.g., a seizure focus of brain 28). Conversely, in the case of Alzheimer's disease, IMD 16 may deliver therapy to a region of brain 28 via electrodes 24, 26 to increase cortical activity within the anterior thalamic nucleus, hippocampus, or other brain region associated with Alzheimer's disease. As another example, in the case of depression (e.g., MDD), IMD 16 may deliver therapy to a region of brain 28 via electrodes 24, 26 to increase cortical activity within one or more regions of brain 28 to effectively treat the patient disorder. As another example, IMD 16 may deliver therapy to a region of brain 28 via electrodes 24, 26 to decrease cortical activity within one or more regions of brain 28, such as, e.g., the frontal cortex, to treat the disorder.

Although leads 20 are shown in FIG. 1 as being coupled to a common lead extension 18, in other examples, leads 20 may be coupled to IMD 16 via separate lead extensions or directly coupled to IMD 16. Moreover, although FIG. 1 illustrates system 10 as including two leads 20A and 20B coupled to IMD 16 via lead extension 18, in some examples, system 10 may include one lead or more than two leads.

Leads 20 may be implanted within a desired location of brain 28 via any suitable technique, such as through respective burr holes in the skull of patient 12 or through a common burr hole in the cranium 32. Leads 20 may be placed at any location within brain 28 such that electrodes 24, 26 of leads 20 are capable of providing electrical stimulation to targeted tissue during treatment. Electrical stimulation generated from the stimulation generator (not shown) within the therapy module of IMD 16 may help mitigate the symptoms of movement disorders, such as by improving the performance of motor tasks by patient 12 that may otherwise be difficult. These tasks may include, for example, at least one of initiating movement, maintaining movement, grasping and moving objects, improving gait and balance associated with narrow turns, and the like. The exact therapy parameter values of the electrical stimulation therapy that may help mitigate symptoms of the movement disorder (or other patient condition) may be specific for the particular target stimulation site (e.g., the region of the brain) involved as well as the particular patient and patient condition.

In the examples shown in FIG. 1, electrodes 24, 26 of leads 20 are shown as ring electrodes. Ring electrodes may be relatively easy to program and are typically capable of delivering an electrical field to any tissue adjacent to leads 20. In other examples, electrodes 24, 26 of leads 20 may have different configurations. For example, electrodes 24, 26 of leads 20 may have a complex electrode array geometry that is capable of producing shaped electrical fields, including interleaved stimulation. An example of a complex electrode array geometry, may include an array of electrodes positioned at different axial positions along the length of a lead, as well as at different angular positions about the periphery, e.g., circumference, of the lead. The complex electrode array geometry may include multiple electrodes (e.g., partial ring or segmented electrodes) around the perimeter of each lead 20, in addition to, or instead of, a ring electrode. In this manner, electrical stimulation may be directed to a specific direction from leads 20 to enhance therapy efficacy and reduce possible adverse side effects from stimulating a large volume of tissue. In some examples in which multiple leads 20 are implanted on the same hemisphere surrounding a target, steered electrical stimulation can be performed in between two or more electrodes.

In some examples, outer housing 34 of IMD 16 may include one or more stimulation and/or sensing electrodes. For example, housing 34 can comprise an electrically conductive material that is exposed to tissue of patient 12 when IMD 16 is implanted in patient 12, or an electrode can be attached to housing 34. In other examples, leads 20 may have shapes other than elongated cylinders as shown in FIG.

1 with active or passive tip configurations. For example, leads 20 may be paddle leads, spherical leads, bendable leads, or any other type of shape effective in treating patient 12.

IMD 16 may deliver electrical stimulation therapy to brain 28 of patient 12 according to one or more stimulation therapy programs. A stimulation therapy program may define one or more electrical stimulation parameter values for therapy generated by a therapy module of IMD 16 and delivered from IMD 16 to brain 28 of patient 12. Where IMD 16 delivers electrical stimulation in the form of electrical pulses, for example, the electrical stimulation parameters may include amplitude mode (constant current or constant voltage with or without multiple independent paths), pulse amplitude, pulse rate, pulse width, a waveform shape, and cycling parameters (e.g., with our without cycling, duration of cycling, and the like). In addition, if different electrodes are available for delivery of stimulation, a therapy parameter of a therapy program may be further characterized by an electrode combination, which may define selected electrodes and their respective polarities.

In some examples, IMD 16 is configured to deliver electrical stimulation therapy to brain 28 of patient 12 in an open loop manner, in which IMD 16 delivers the stimulation therapy without intervention from a user or a sensor. In other examples, IMD 16 is configured to deliver electrical stimulation therapy to brain 28 of patient 12 in a closed loop manner or a pseudo-closed loop manner, in which IMD 16 controls the timing of the delivery of electrical stimulation to brain 28, the output parameters of the electrical stimulation, or both based on one or more of user input and input from a sensor. The sensor may, for example, provide feedback that may be used to control the electrical stimulation output from IMD 16.

In addition to being configured to deliver therapy to manage a disorder of patient 12, therapy system 10 is configured to sense bioelectrical brain signals of patient 12. For example, IMD 16 may include a sensing module that is configured to sense bioelectrical brain signals within one or more regions of brain 28 via a subset of electrodes 24, 26, another set of electrodes, or both. Accordingly, in some examples, electrodes 24, 26 may be used to deliver electrical stimulation from the therapy module to target sites within brain 28 as well as sense brain signals within brain 28. However, IMD 16 can also use a separate set of sensing electrodes to sense the bioelectrical brain signals. In the example shown in FIG. 1, the signals generated by electrodes 24, 26 are conducted to the sensing module within IMD 16 via conductors within the respective lead 20A, 20B. In some examples, the sensing module of IMD 16 may sense bioelectrical brain signals via one or more of the electrodes 24, 26 that are also used to deliver electrical stimulation to brain 28. In other examples, one or more of electrodes 24, 26 may be used to sense bioelectrical brain signals while one or more different electrodes 24, 26 may be used to deliver electrical stimulation.

Depending on the particular stimulation electrodes and sense electrodes used by IMD 16, IMD 16 may monitor bioelectrical brain signals and deliver electrical stimulation at the same region of brain 28 or at different regions of brain 28. In some examples, the electrodes used to sense bioelectrical brain signals may be located on the same lead used to deliver electrical stimulation, while in other examples, the electrodes used to sense bioelectrical brain signals may be located on a different lead than the electrodes used to deliver electrical stimulation. In some examples, a bioelectrical brain signal of patient 12 may be monitored with external electrodes, e.g., scalp electrodes. Moreover, in some examples, the sensing module that senses bioelectrical brain signals of brain 28 (e.g., the sensing module that generates an electrical signal indicative of the activity within brain 28) is in a physically separate housing from outer housing 34 of IMD 16. However, in the example shown in FIG. 1 and the example primarily referred to herein for ease of description, the sensing module and therapy module of IMD 16 are enclosed within a common outer housing 34.

The bioelectrical brain signals sensed by IMD 16 may reflect changes in electrical current produced by the sum of electrical potential differences across brain tissue. Example bioelectrical brain signals include, but are not limited to, an electroencephalogram (EEG) signal, an electrocorticogram (ECoG) signal, a LFP sensed from within one or more regions of a patient's brain, and/or action potentials from single cells within the patient's brain. In some examples, LFP data can be measured ipsilaterally or contralaterally and considered as an average (e.g., a maximum or minimum or a heuristic combination thereof) or as some other value. The location at which the signals are obtained may be adjusted to a disease onset side of the body of patient 12 or severity of symptoms or disease duration. The adjustments, may, for example, be made on the basis of clinical symptoms presented and their severity, which can be augmented or annotated with recorded LFP data. A clinician or a processor of IMD 16 may also add heuristic weights to ipsilaterally and/or contralaterally measured LFP data to be considered for system feedback.

Sensed bioelectrical brain signals of patient 12 may be used to determine the patient state of patient 12. The patient state can be, for example, a patient disease state, a state in which a symptom of a patient condition is observed, or a patient state indicative of the efficacy of therapy delivered by a medical device or the efficacy of medication. As discussed in further detail below, e.g., with respect to FIG. 4, in some examples, a processor of programmer 14, IMD 16, or another device, alone or in combination with each other, determines a patient state based on activity of a bioelectrical brain signal of the patient in one or more frequency sub-bands of a frequency band of interest. For example, the processor may determine a patient state based on the power level in one or more particular more frequency sub-bands of a frequency band of interest of a bioelectrical brain signal sensed by IMD 16, based on the spectral patterns of the bioelectrical brain signal (e.g., a shift in in peak power level from one frequency sub-band to another over time), or any combination thereof. The processor may determine the patient state by, for example, receiving a sensed bioelectrical brain signal and detecting a predetermined biomarker indicative of a particular patient state, the biomarker including one or more spectral characteristics associated with the particular patient state.

In some examples, the processor generates an indication of the determined patient state, controls therapy delivery to the patient based on the determined patient state, monitors a patient condition based on the determined patient state, generates a patient diagnosis (e.g., determines a patient condition sub-type) based on the determined patient state, or any combination thereof. For example, the processor can control therapy delivery by, for example, modifying one or more therapy parameter values based on the determined patient state. One or more therapy parameter values may be controlled in order to increase or decrease the intensity of therapy delivery (e.g., by increasing or decreasing one or more of the frequency, amplitude, or other stimulation parameter values), to initiate delivery of electrical stimulation, by IMD 16, to a target therapy delivery site in patient 12, or, depending on the type of therapy delivery, to terminate delivery of electrical stimulation to the target therapy delivery site.

The processor may modify the therapy delivered by IMD 16 using any suitable technique. In some examples, the processor modifies therapy by at least modifying at least one therapy parameter value with which IMD 16 generates and delivers therapy to patient 12. The at least one therapy parameter value may be a part of a therapy program that defines values for a plurality of therapy parameters. As a result, in some examples, the processor may modify at least one therapy parameter value by at least modifying a therapy program (e.g., changing the value of at least one therapy parameter of the therapy program or selecting a new therapy program).

In some examples, IMD 16 may be configured to sense the bioelectrical brain signal (e.g., by measuring a LFP) at periodic, predetermined (which may also be periodic), or random intervals, or in response to a patient input or another trigger. In other examples, IMD 16 continuously senses the bioelectrical brain signal, but the processor only samples the sensed bioelectrical brain signal (e.g., the last stored bioelectrical brain signal) and determines whether the sample includes the biomarker at predetermined periodic times or in response to user input (e.g., input/trigger from a patient).

External programmer 14 is configured to wirelessly communicate with IMD 16 as needed to provide or retrieve therapy information. Programmer 14 is an external computing device that the user, e.g., the clinician and/or patient 12, may use to communicate with IMD 16. For example, programmer 14 may be a clinician programmer that the clinician uses to communicate with IMD 16 and program one or more therapy programs for IMD 16. In addition, or instead, programmer 14 may be a patient programmer that allows patient 12 to select programs and/or view and modify therapy parameter values. The clinician programmer may include more programming features than the patient programmer. In other words, more complex or sensitive tasks may only be allowed by the clinician programmer to prevent an untrained patient from making undesired changes to IMD 16.

Programmer 14 may be a hand-held computing device with a display viewable by the user and an interface for providing input to programmer 14 (i.e., a user input mechanism). For example, programmer 14 may include a small display screen (e.g., a liquid crystal display (LCD) or a light emitting diode (LED) display) that presents information to the user. In addition, programmer 14 may include a touch screen display, keypad, buttons, a peripheral pointing device or another input mechanism that allows the user to navigate though the user interface of programmer 14 and provide input. If programmer 14 includes buttons and a keypad, the buttons may be dedicated to performing a certain function, i.e., a power button, the buttons and the keypad may be soft keys that change in function depending upon the section of the user interface currently viewed by the user, or any combination thereof. Alternatively, the screen (not shown) of programmer 14 may be a touch screen that allows the user to provide input directly to the user interface shown on the display. The user may use a stylus or their finger to provide input to the display.

In other examples, programmer 14 may be a larger workstation or a separate application within another multi-function device, rather than a dedicated computing device. For example, the multi-function device may be a notebook computer, tablet computer, workstation, cellular phone, personal digital assistant or another computing device that may run an application that enables the computing device to operate as a secure medical device programmer 14. A wireless adapter coupled to the computing device may enable secure communication between the computing device and IMD 16.

When programmer 14 is configured for use by the clinician, programmer 14 may be used to transmit initial programming information to IMD 16. This initial information may include hardware information, such as the type of leads 20, the arrangement of electrodes 24, 26 on leads 20, the position of leads 20 within brain 28, initial programs defining therapy parameter values, and any other information that may be useful for programming into IMD 16. Programmer 14 may also be capable of completing functional tests (e.g., measuring the impedance of electrodes 24, 26 of leads 20).

The clinician may also generate and store therapy programs within IMD 16 with the aid of programmer 14. During a programming session, the clinician may determine one or more therapy programs that may provide efficacious therapy to patient 12 to address symptoms associated with the movement disorder (or other patient conditions). For example, the clinician may select one or more electrode combinations with which stimulation is delivered to brain 28. During the programming session, patient 12 may provide feedback to the clinician as to the efficacy of the specific program being evaluated or the clinician may evaluate the efficacy based on one or more sensed or observable physiological parameters of patient (e.g., muscle activity) or based on motion detected via one or more motion sensors that generate signals indicative of motion of patient 12. Programmer 14 may assist the clinician in the creation/identification of therapy programs by providing a methodical system for identifying potentially beneficial therapy parameter values.

Programmer 14 may also be configured for use by patient 12. When configured as a patient programmer, programmer 14 may have limited functionality (compared to a clinician programmer) in order to prevent patient 12 from altering critical functions of IMD 16 or applications that may be detrimental to patient 12.

Whether programmer 14 is configured for clinician or patient use, programmer 14 is configured to communicate to IMD 16 and, optionally, another computing device, via wireless communication. Programmer 14, for example, may communicate via wireless communication with IMD 16 using radio frequency (RF) telemetry techniques known in the art. Programmer 14 may also communicate with another programmer or computing device via a wired or wireless connection using any of a variety of local wireless communication techniques, such as RF communication according to the 802.11 or Bluetooth specification sets, infrared (IR) communication according to the IRDA specification set, or other standard or proprietary telemetry protocols. Programmer 14 may also communicate with other programming or computing devices via exchange of removable media, such as magnetic or optical disks, memory cards or memory sticks. Further, programmer 14 may communicate with IMD 16 and another programmer via remote telemetry techniques known in the art, communicating via a local area network (LAN), wide area network (WAN), public switched telephone network (PSTN), or cellular telephone network, for example.

Therapy system 10 may be implemented to provide chronic stimulation therapy to patient 12 over the course of several months or years. However, system 10 may also be employed on a trial basis to evaluate therapy before committing to full implantation. If implemented temporarily, some components of system 10 may not be implanted within patient 12. For example, patient 12 may be fitted with an external medical device, such as a trial stimulator, rather than IMD 16. The external medical device may be coupled to percutaneous leads or to implanted leads via a percutaneous extension. If the trial stimulator indicates DBS system 10 provides effective treatment to patient 12, the clinician may implant a chronic stimulator within patient 12 for relatively long-term treatment.

System 10 shown in FIG. 1 is merely one example of a therapy system that is configured to determine a patient state based on activity of a bioelectrical brain signal of patient 12 in one or more frequency sub-bands of a frequency band. Systems with other configurations of leads, electrodes, and sensors are possible. For example, in other implementations, IMD 16 may be coupled to additional leads or lead segments having one or more electrodes positioned at different target tissue sites, which may be within brain 28 or outside of brain (e.g., proximate to a spinal cord of patient 12, a peripheral nerve of patient 12, a muscle of patient 12, or any other suitable therapy delivery site). The additional leads may be used for delivering different stimulation therapies to respective stimulation sites within patient 12 or for monitoring at least one physiological parameter of patient 12.

Additionally, in other examples, a system may include more than one IMD. For example, a system may include two IMDs coupled to respective one or more leads. Each IMD can deliver stimulation to a respective lateral side of patient 12 in some examples.

As another example configuration, a therapy system can include one or more leadless electrical stimulators (e.g., microstimulators having a smaller form factor than IMD 16 and may not be coupled to any separate leads). The leadless electrical stimulators can be configured to generate and deliver electrical stimulation therapy to patient 12 via one or more electrodes on an outer housing of the electrical stimulator. In examples including a plurality of leadless electrical stimulators, the leadless electrical stimulators can be implanted at different target tissue sites within patient 12. One electrical stimulator may act as a "master" module that coordinates the delivery of stimulation to patient 12 via the plurality of electrical stimulators.

In some examples, IMD 16 is not configured to delivery electrical stimulation therapy to brain of patient 12, but, rather, is only configured to sense one or more physiological parameters of patient 12, including a bioelectrical brain signal of patient 12. This type of IMD 16 may a patient monitoring device useful for diagnosing patient 12, monitoring a patient condition 12, or to train IMD 16 or another IMD for therapy delivery. For example, during a learning phase, a processor of IMD 16 or another processor can determine, based on the oscillation spectra of a bioelectrical brain signal sensed by IMD 16, spectral characteristics of a bioelectrical brain signal indicative of one or more specific patient states (e.g., normal brain function, abnormal brain function, specific patient symptoms, patient, a movement state, a sleep state, a speech state, and the like). Example spectral characteristics include, for example, power levels in one or more frequency sub-bands, spectral patterns (e.g., a pattern in the activity in one or more frequency sub-bands over time), or any combination thereof. These spectral characteristics may be, for example, stored by programmer 14, IMD 16, or another device as biomarkers indicative of a particular patient state, such as normal or pathological behaviors, responses to medications or other therapies, including electrical therapies, or both.

Figure 2:
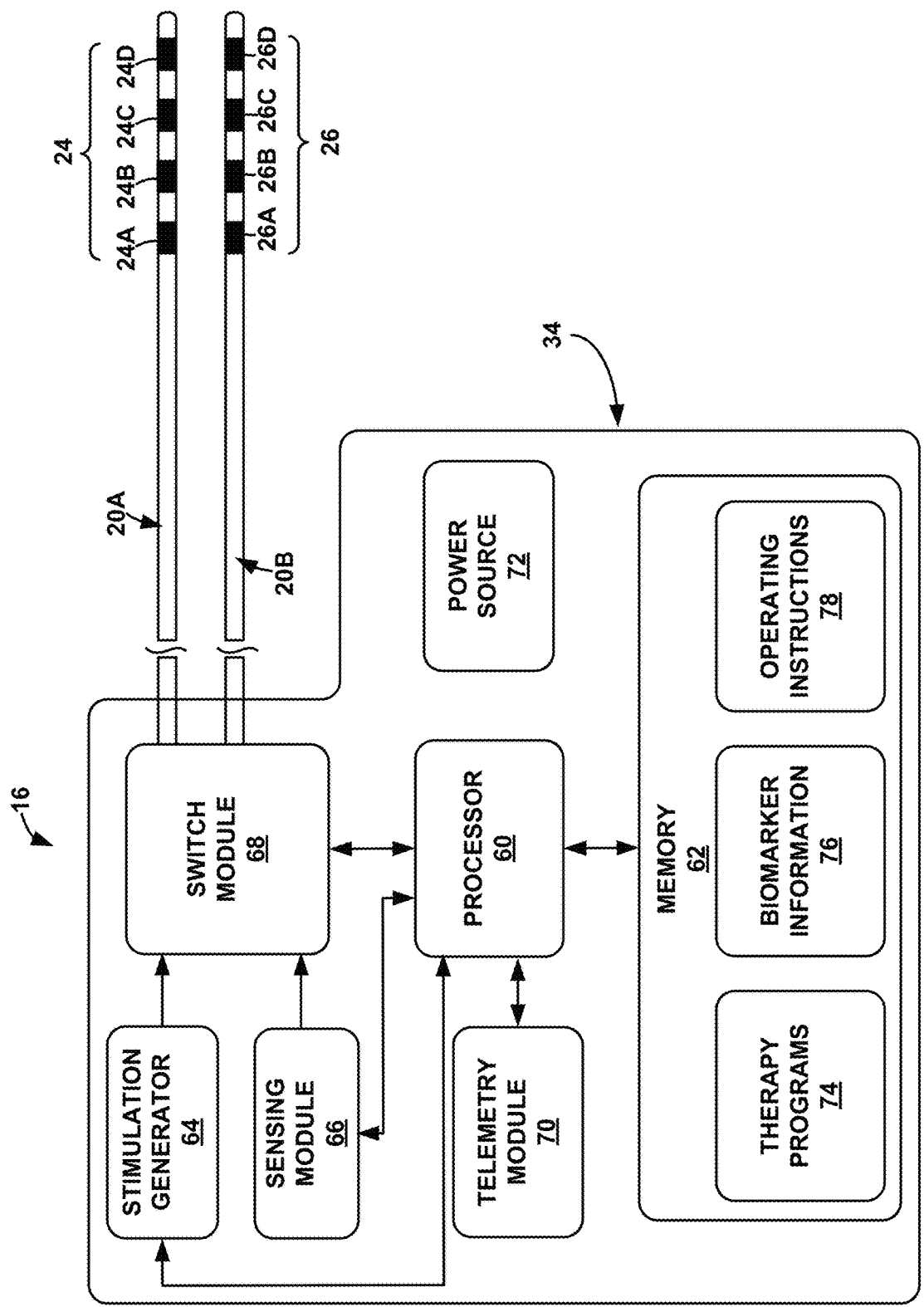
FIG. 2 is functional block diagram illustrating components of an example medical device.

FIG. 2 is functional block diagram illustrating components of an example IMD 16. In the example shown in FIG. 2, IMD 16 includes processor 60, memory 62, stimulation generator 64, sensing module 66, switch module 68, telemetry module 70, and power source 72. Memory 62, as well as other memories described herein, may include any volatile or non-volatile media, such as a random access memory (RAM), read only memory (ROM), non-volatile RAM (NVRAM), electrically erasable programmable ROM (EEPROM), flash memory, and the like. Memory 62 may store computer-readable instructions that, when executed by processor 60, cause IMD 16 to perform various functions described herein.

In the example shown in FIG. 2, memory 62 stores therapy programs 74, biomarker information 76, and operating instructions 78, e.g., in separate memories within memory 62 or separate areas within memory 62. Each stored therapy program 74 defines a particular program of therapy in terms of respective values for electrical stimulation parameters, such as a stimulation electrode combination, electrode polarity, current or voltage amplitude, and, if stimulation generator 64 generates and delivers stimulation pulses, the therapy programs may define values for a pulse width, and pulse rate of a stimulation signal. Each stored therapy program 74 may also be referred to as a set of therapy parameter values. In some examples, the therapy programs may be stored as a therapy group, which defines a set of therapy programs with which stimulation may be generated. The stimulation signals defined by the therapy programs of the therapy group may be delivered together on an overlapping or non-overlapping (e.g., time-interleaved) basis.

Biomarker information 76 stored by memory 62 includes one or more spectral characteristics indicative of a particular patient state. In some examples, each biomarker is associated with a patient state. Each patient state of a plurality of patient states can be associated with one or more respective biomarkers. In other examples, each patient state of a plurality of patient states is associated with one respective biomarker. Stored biomarkers include biomarkers that indicate activity of a bioelectrical brain signal of a patient in one or more frequency sub-bands of a frequency band of interest. For example, biomarker information 76 may store one or more biomarkers that indicate a spectral pattern of a bioelectrical brain signal in a frequency band of interest, such as a pattern in the power distribution between sub-bands of the frequency band over time. An example pattern in the power distribution that may be stored as a biomarker includes a shift in a power distribution (e.g., a peak power or highest relative average power) between sub-bands of the frequency band over time, such as a shift of the peak power from a frequency of about 15 Hz to a frequency of about 20 Hz, where 15 Hz and 20 Hz are in different frequency sub-bands, or a shift from an average peak power for a frequency sub-band from a first frequency sub-band (e.g., about 19 Hz to about 21 Hz) to a second frequency sub-band (e.g., about 13 Hz to about 18 Hz). Other examples pattern in the power distribution that may be stored as a biomarker includes the frequency sub-band in which a peak power within a frequency band of interest is observed, or the frequency sub-band in which a peak power of the overall peak power level of the bioelectrical brain signal is observed. The frequency sub-bands may be predefined prior to any automatic patient state detection by IMD 16.

In addition, or instead, a spectral pattern of a bioelectrical brain signal stored by biomarker information 76 as a biomarker for a particular patient state may include a change in the sub-band having the peak frequency or dominant activity, such as a shift from one particular frequency sub-band to another. A spectral pattern of a bioelectrical brain signal stored by biomarker information 76 as a biomarker for a particular patient state may include a pattern of the power distribution over one or more frequency sub-bands (e.g., a narrow peak, a broad peak, a unimodal peak, or a bimodal peak), or a width or a variability (e.g., in the width) of one or more frequency sub-bands exhibiting a relatively high or low level of activity, e.g., relative to a predetermined threshold of such activity. Any combination of the spectral patterns may be stored as biomarker information 76.

The frequency sub-band exhibiting the relatively high activity can be, for example, the frequency sub-band having the dominant activity in the frequency band of interest or having an activity level greater than or equal to a threshold value. The frequency sub-band exhibiting the relatively low activity can be, for example, the frequency sub-band having the lowest amount of activity in the frequency band of interest or having an activity level less than or equal to a threshold value. It is believed that in some cases, a frequency sub-band exhibiting the relatively high activity may be indicative of a sub-type of the patient condition, such as a sub-type of Parkinson's disease. For example, a dominant amount of beta band activity in a relatively low frequency sub-band of the beta band may indicate a different type of Parkinson's disease than a dominant amount of beta band activity in a relatively high frequency sub-band of the beta band.

It is believed that in some cases, a characteristic of a distribution of a signal strength (also referred to herein as a "power distribution") may be indicative of a sub-type of the patient condition, such as a sub-type of Parkinson's disease, or another patient state. The signal strength distribution can be determined, e.g., by a processor of a device, based on a plot of a power level versus frequency of the frequency domain characteristics of the bioelectrical brain signal. In some examples, a predetermined characteristic of a distribution of a signal strength within the frequency band of the bioelectrical brain signal indicative of a patient state can include a shape of the peak of the plot. For example, a relatively sharp peak (e.g., a peak having a width less than, or less than or equal to, a threshold value) may be associated with a different type of Parkinson's disease than a relatively broad peak (e.g., a peak having a greater less than, or greater than or equal to, a threshold value). The width of a peak of the frequency domain plot of the bioelectrical brain signal can be measured in units of Hertz (e.g., indicating the frequency span of the peak), and can be determined to be the width (as indicated by the frequency span) from one point at a particular percentage of the peak power (e.g., about 90% of the peak power) to another point at the particular percentage of the peak power. For example, the width of a peak can be the width from a point that is 90% of the peak power to the next point that is 90% of the peak power (and at a different frequency).

As another example, a unimodal peak may be associated with a different type of Parkinson's disease than a bimodal peak. Thus, biomarker information 76 may store one or more biomarkers indicative of and associated with these different sub-types of a patient condition. Detection of a particular biomarker may, therefore, but useful for diagnosing a patient.

Processor 60 (or processor of another device, such as programmer 14) can determine a biomarker that indicates a power distribution of a bioelectrical brain signal based on a waveform generated from a plot of the power level versus frequency. The biomarker can be, for example, any parameters that indicate a specific pattern in the power distribution. For example, the biomarker can be a template signal stored by memory 62. Processor 60 can detect such a biomarker in a sensed bioelectrical brain signal by, for example, correlating the sensed bioelectrical brain signal with the template signal and detecting the biomarker in response to determining there is a substantial correlation (e.g., about 80%, about 90%, or about 95% or more) between a sensed bioelectrical brain signal and the template signal.

As another example, the biomarker can be a difference in the power distribution relative to a baseline bioelectrical brain signal. In some examples, the baseline bioelectrical brain signal can be, for example, a signal that indicates a patient state in which no therapeutic effects of the therapy are observed (e.g., a pathological state) or a state in which no patient symptoms are observed. In either case, the baseline bioelectrical brain signal may be patient-specific or may be more general to a plurality of patients.

As another example, biomarker information 76 may store one or more biomarkers that indicate the power level of a bioelectrical brain signal of the patient in one or more frequency sub-bands of a frequency band or a threshold power level associated with a patient state. For example, a power level greater than or equal to a threshold value in a particular frequency sub-band may be associated with a particular patient state. As another example, a power level less than or equal to a threshold value in a particular frequency sub-band may be associated with a particular patient state.

In any of these examples, the particular characteristics of a biomarker may vary between patients, as well as may vary depending on the area of brain 28 in which the electrodes 24, 26 used to sense the bioelectrical brain signal are implanted, which may depend on the depth of the electrodes 24, 26 in brain 28.

In some examples, memory 62 may also store brain signal data generated by sensing module 66 via at least one of electrodes 24, 26 and, in some cases, at least a portion of outer housing 34 of IMD 16, an electrode on outer housing 34 of IMD 16 or another reference. In addition, in some examples, processor 60 may append a time and date stamp to the brain signal data in memory 62. Operating instructions 78 guide general operation of IMD 16 under control of processor 60, and may include instructions for monitoring brains signals within one or more brain regions via electrodes 24, 26 and delivering electrical stimulation therapy to patient 12.

Stimulation generator 64, under the control of processor 60, generates stimulation signals for delivery to patient 12 via selected combinations of electrodes 24, 26. In some examples, stimulation generator 64 generates and delivers stimulation signals to one or more target regions of brain 28 (FIG. 1), via a select combination of electrodes 24, 26, based on one or more stored therapy programs 74. The target tissue sites within brain 28 for stimulation signals or other types of therapy and stimulation parameter values may depend on the patient condition for which therapy system 10 is implemented to manage. While stimulation pulses are described, stimulation signals may be of any form, such as continuous-time signals (e.g., sine waves) or the like.

The processors described in this disclosure, including processor 60, may include one or more digital signal processors (DSPs), general purpose microprocessors, application specific integrated circuits (ASICs), field programmable logic arrays (FPGAs), or other equivalent integrated or discrete logic circuitry, or combinations thereof. The functions attributed to processors described herein may be provided by a hardware device and embodied as software, firmware, hardware, or any combination thereof. Processor 60 is configured to control stimulation generator 64 according to therapy programs 74 stored by memory 62 to apply particular stimulation parameter values specified by one or more programs, such as amplitude, pulse width, and pulse rate.

In the example shown in FIG. 2, the set of electrodes 24 of lead 20A includes electrodes 24A, 24B, 24C, and 24D, and the set of electrodes 26 of lead 20B includes electrodes 26A, 26B, 26C, and 26D. Processor 60 may control switch module 68 to apply the stimulation signals generated by stimulation generator 64 to selected combinations of electrodes 24, 26. In particular, switch module 68 may couple stimulation signals to selected conductors within leads 20, which, in turn, deliver the stimulation signals across selected electrodes 24, 26. Switch module 68 may be a switch array, switch matrix, multiplexer, or any other type of switching module configured to selectively couple stimulation energy to selected electrodes 24, 26 and to selectively sense bioelectrical brain signals with selected electrodes 24, 26. Hence, stimulation generator 64 is coupled to electrodes 24, 26 via switch module 68 and conductors within leads 20. In some examples, however, IMD 16 does not include switch module 68.

Stimulation generator 64 may be a single channel or multi-channel stimulation generator. In particular, stimulation generator 64 may be capable of delivering, a single stimulation pulse, multiple stimulation pulses or continuous signal at a given time via a single electrode combination or multiple stimulation pulses at a given time via multiple electrode combinations. In some examples, however, stimulation generator 64 and switch module 68 may be configured to deliver multiple channels on a time-interleaved basis. For example, switch module 68 may serve to time divide the output of stimulation generator 64 across different electrode combinations at different times to deliver multiple programs or channels of stimulation energy to patient 12.

Sensing module 66, under the control of processor 60, is configured to sense bioelectrical brain signals of patient 12 via a selected subset of electrodes 24, 26 or with one or more electrodes 24, 26 and at least a portion of a conductive outer housing 34 of IMD 16, an electrode on an outer housing of IMD 16 or another reference. Processor 60 may control switch module 68 to electrically connect sensing module 66 to selected electrodes 24, 26. In this way, sensing module 66 may selectively sense bioelectrical brain signals with different combinations of electrodes 24, 26 (and/or a reference other than an electrode 24, 26). As previously described, processor 60 may monitor the efficacy of therapy delivery by IMD 16 via the sensed bioelectrical brain signals and determine whether the efficacy of therapy delivery has changed, and, in response, generate a notification (e.g., to patient 12 or patient caretaker).

In some examples, sensing module 66 includes a frequency selective sensing circuit that extracts the energy level within one or more selected frequency bands and sub-bands of a sensed patient parameter signal, which may be, for example, a bioelectrical brain signal. The frequency selective sensing circuit can include a chopper-stabilized superheterodyne instrumentation amplifier and a signal analysis unit, and may utilize a heterodyning, chopper-stabilized amplifier architecture to convert a selected frequency band (or frequency sub-band) of a physiological signal, such as a bioelectrical brain signal, to a baseband for analysis. The physiological signal may be analyzed in one or more selected frequency bands to determine one or more features as described herein. In some examples, sensing module 66 includes a plurality of channels that extract the same or different frequency bands (or sub-bands) of one or more signals indicative of one or more patient parameters.

Examples of various additional chopper amplifier circuits that may be suitable for or adapted to the techniques, circuits and devices of this disclosure are described in U.S. Pat. No. 7,385,443 to Denison, which is entitled "CHOPPER STABILIZED INSTRUMENTATION AMPLIFIER" and issued on Jan. 10, 2008, the entire content of which is incorporated herein by reference. Examples of frequency selective monitors that may utilize a heterodyning, chopper-stabilized amplifier architecture are described in U.S. Provisional Application No. 60/975,372 by Denison et al., entitled "FREQUENCY SELECTIVE MONITORING OF PHYSIOLOGICAL SIGNALS," and filed on Sep. 26, 2007, commonly-assigned U.S. Provisional Application No. 61/025,503 by Denison et al., entitled "FREQUENCY SELECTIVE MONITORING OF PHYSIOLOGICAL SIGNALS", and filed on Feb. 1, 2008, and commonly-assigned U.S. Provisional Application No. 61/083,381, entitled, "FREQUENCY SELECTIVE EEG SENSING CIRCUITRY," and filed on Jul. 24, 2008. The entire contents of above-identified U.S. Provisional Application Nos. 60/975,372, 61/025,503, and 61/083,381 are incorporated herein by reference. Further examples of chopper amplifier circuits are also described in further detail in commonly-assigned U.S. Patent Application Publication No. 2009/0082691 by Denison et al., entitled, "FREQUENCY SELECTIVE MONITORING OF PHYSIOLOGICAL SIGNALS" and filed on Sep. 25, 2008. U.S. Patent Application Publication No. 2009/0082691 by Denison et al. is incorporated herein by reference in its entirety.

A sensing module 66 that directly extracts energy in key frequency bands of a bioelectrical brain signal may be used to extract bandpower at key physiological frequencies with an architecture that is flexible, robust, and relatively low-noise. Chopper stabilization is a noise and power efficient architecture for amplifying low-frequency physiological signals in micropower applications (e.g., an implanted device) with excellent process immunity. Chopper stabilized amplifiers can be adapted to provide wide dynamic range, high-Q filters. A sensing module 66 that includes a chopper-stabilized amplifier may slightly displace the clocks within the chopper amplifier in order to re-center a targeted band of energy to direct current (DC) in a manner similar to superheterodyne receivers used in communication systems. In some examples, extracting the bandpower within a selected frequency band requires two parallel signal paths (in-phase and quadrature) that are combined within the power extraction stage. The power output signal can be lowpass filtered, which results in an output that represents the spectral power fluctuations in the frequency band.

As previously indicated, a bioelectrical brain signal may include an EEG, ECoG, single cell recording, or LFP. The band power fluctuations in LFPs sensed within brain 28 of patient 12 (FIG. 1) can be orders of magnitude slower than the frequency at which they are encoded, so the use of efficient analog preprocessing before performing analog to digital conversion can greatly reduce the overall energy requirements for implementing a complete mixed-signal system. Thus, a sensing module 66 that includes a circuit architecture that directly extracts energy in key frequency bands (or sub-bands) of a bioelectrical brain signal may be useful for tracking the relatively slow power fluctuations within the selected frequency bands and determining a patient state based on the bioelectrical brain signal.

Although sensing module 66 is incorporated into a common housing 34 with stimulation generator 64 and processor 60 in FIG. 2, in other examples, sensing module 66 is in a separate outer housing from outer housing 34 of IMD 16 and communicates with processor 60 via wired or wireless communication techniques.

In some examples, processor 60 (or another processor of system 10) may be configured to modify therapy delivered by IMD 16 in response to detecting a biomarker in a bioelectrical brain signal sensed by sensing module 66. In this way, a bioelectrical brain signal sensed by sensing module 66 may be used for closed-loop control of electrical stimulation delivery by IMD 16.

Telemetry module 70 is configured to support wireless communication between IMD 16 and an external programmer 14 or another computing device under the control of processor 60. Processor 60 of IMD 16 may receive, as updates to programs, values for various stimulation parameters such as amplitude and electrode combination, from programmer 14 via telemetry module 70. The updates to the therapy programs may be stored within therapy programs 74 portion of memory 62. Telemetry module 70 in IMD 16, as well as telemetry modules in other devices and systems described herein, such as programmer 14, may accomplish communication by RF communication techniques. In addition, telemetry module 70 may communicate with external medical device programmer 14 via proximal inductive interaction of IMD 16 with programmer 14. Accordingly, telemetry module 70 may send information to external programmer 14 on a continuous basis, at periodic intervals, or upon request from IMD 16 or programmer 14. For example, processor 60 may transmit brain state information 76 to programmer 14 via telemetry module 70.

Power source 72 delivers operating power to various components of IMD 16. Power source 72 may include a small rechargeable or non-rechargeable battery and a power generation circuit to produce the operating power. Recharging may be accomplished through proximal inductive interaction between an external charger and an inductive charging coil within IMD 16. In some examples, power requirements may be small enough to allow IMD 16 to utilize patient motion and implement a kinetic energy-scavenging device to trickle charge a rechargeable battery. In other examples, traditional batteries may be used for a limited period of time.

Figure 3:
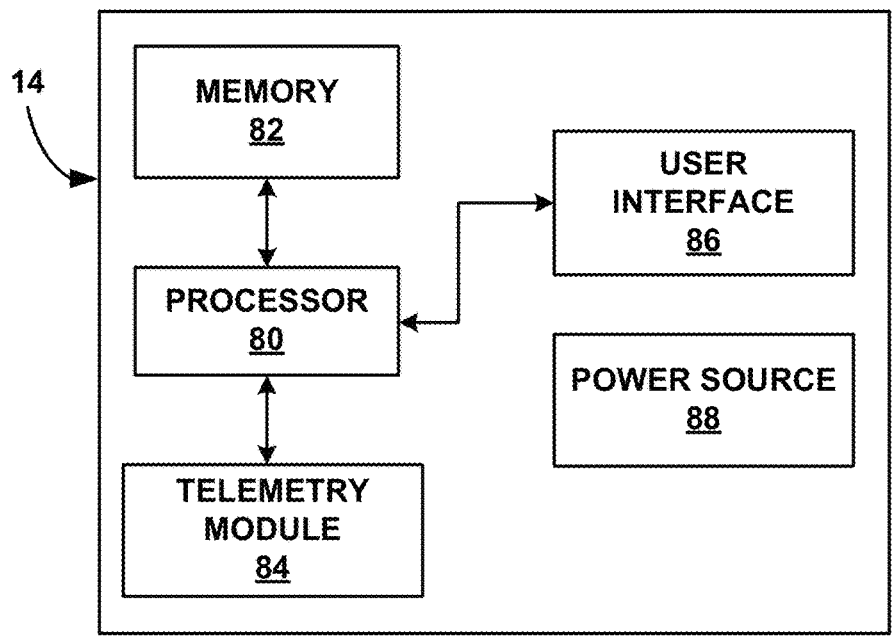
FIG. 3 is a functional block diagram illustrating components of an example medical device programmer.

FIG. 3 is a functional block diagram illustrating components of an example medical device programmer 14 (FIG. 1). Programmer 14 includes processor 80, memory 82, telemetry module 84, user interface 86, and power source 88. Processor 80 controls user interface 86 and telemetry module 84, and stores and retrieves information and instructions to and from memory 82. Programmer 14 may be configured for use as a clinician programmer or a patient programmer. Processor 80 may comprise any combination of one or more processors including one or more microprocessors, DSPs, ASICs, FPGAs, or other equivalent integrated or discrete logic circuitry. Accordingly, processor 80 may include any suitable structure, whether in hardware, software, firmware, or any combination thereof, to perform the functions ascribed herein to processor 80.

A user, such as a clinician or patient 12, may interact with programmer 14 through user interface 86. User interface 86 includes a display (not shown), such as a LCD or LED display or other type of screen, with which processor 80 may present information related to the therapy, a patient condition detected by programmer 14 or IMD 16 based on a frequency domain characteristic of a sensed bioelectrical brain signal, or electrical signals sensed via a plurality of sense electrode combinations. In addition, user interface 86 may include an input mechanism to receive input from the user. The input mechanisms may include, for example, buttons, a keypad (e.g., an alphanumeric keypad), a peripheral pointing device or another input mechanism that allows the user to navigate though user interfaces presented by processor 80 of programmer 14 and provide input.

If programmer 14 includes buttons and a keypad, the buttons may be dedicated to performing a certain function, i.e., a power button, or the buttons and the keypad may be soft keys that change function depending upon the section of the user interface currently viewed by the user. In addition, or instead, the screen (not shown) of programmer 14 may be a touch screen that allows the user to provide input directly to the user interface shown on the display. The user may use a stylus or their finger to provide input to the display. In other examples, user interface 86 also includes audio circuitry for providing audible notifications, instructions or other sounds to patient 12, receiving voice commands from patient 12, which may be useful if patient 12 has limited motor functions, or both. Patient 12, a clinician or another user may also interact with programmer 14 to manually select therapy programs, generate new therapy programs, modify therapy programs through individual or global adjustments, and transmit the new programs to IMD 16.

In some examples, at least some of the control of therapy delivery by IMD 16 may be implemented by processor 80 of programmer 14. For example, in some examples, processor 80 may receive sensed brain signal information from IMD 16 or from a sensing module that is separate from IMD 16. The separate sensing module may, but need not be, implanted within patient 12. Brain signal information may include, for example, a raw bioelectrical brain signal, parameterized bioelectrical brain signal, or any other suitable information indicative of a bioelectrical brain signal sensed by sensing module 66. Processor 80 may determine a patient stated based on the received brain signal information, e.g., using any of the techniques described herein. In addition, in some examples, processor 80 may generate an indication of the determined patient state, control therapy delivery by IMD 16 to patient 12 based on the determined patient state, monitor a patient condition based on the determined patient state, generate a patient diagnosis (e.g., determines a patient condition sub-type) based on the determined patient state, or any combination thereof.

Memory 82 may include instructions for operating user interface 86 and telemetry module 84, and for managing power source 88. In some examples, memory 82 may also store any therapy data retrieved from IMD 16 during the course of therapy, biomarker information, sensed bioelectrical brain signals, and the like. In some instances, the clinician may use this therapy data to determine the progression of the patient condition in order to plan future treatment for the movement disorder (or other patient condition) of patient 12. Memory 82 may include any volatile or nonvolatile memory, such as RAM, ROM, EEPROM or flash memory. Memory 82 may also include a removable memory portion that may be used to provide memory updates or increases in memory capacities. A removable memory may also allow sensitive patient data to be removed before programmer 14 is used by a different patient.

Wireless telemetry in programmer 14 may be accomplished by RF communication or proximal inductive interaction of external programmer 14 with IMD 16. This wireless communication is possible through the use of telemetry module 84. Accordingly, telemetry module 84 may be similar to the telemetry module contained within IMD 16. In other examples, programmer 14 may be capable of infrared communication or direct communication through a wired connection. In this manner, other external devices may be capable of communicating with programmer 14 without needing to establish a secure wireless connection.

Power source 88 is configured to deliver operating power to the components of programmer 14. Power source 88 may include a battery and a power generation circuit to produce the operating power. In some examples, the battery may be rechargeable to allow extended operation. Recharging may be accomplished by electrically coupling power source 88 to a cradle or plug that is connected to an alternating current (AC) outlet. In addition, recharging may be accomplished through proximal inductive interaction between an external charger and an inductive charging coil within programmer 14. In other examples, traditional batteries (e.g., nickel cadmium or lithium ion batteries) may be used. In addition, programmer 14 may be directly coupled to an alternating current outlet to operate.

Figure 4:
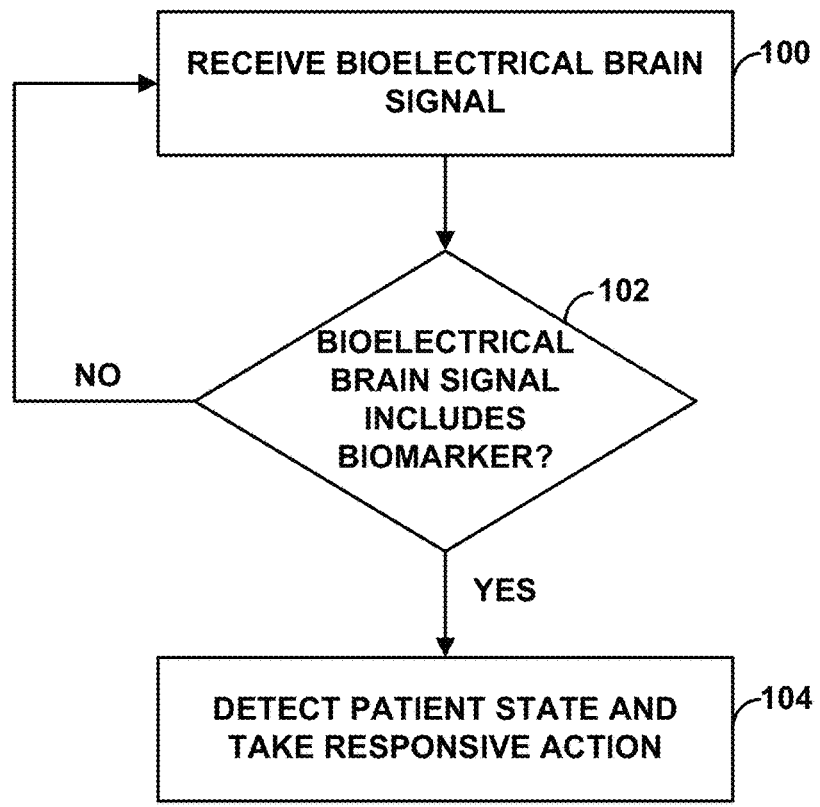
FIG. 4 is a flow diagram illustrating an example technique for determining a patient state based on a sensed bioelectrical brain signal.

FIG. 4 is a flow diagram illustrating an example technique for determining a patient state based on a sensed bioelectrical brain signal and taking a responsive action in response to the determined patient state. While the technique shown in FIG. 4, as well as many other techniques, are described with respect to processor 60 of IMD 16, in other examples, a processor of another device, such as processor 80 of programmer 14 (FIG. 3), can perform any part of the techniques described herein, alone or in combination with another device.

In accordance with the technique shown in FIG. 4, processor 60 of IMD 16 receives a bioelectrical brain signal sensed by sensing module 66 (100). For example, processor 60 may control sensing module 66 to sense a bioelectrical brain signal of patient 12, e.g., via one or more of electrodes 24, 26 on leads 20, and sensing module 66 may transmit the sensed bioelectrical brain signal to processor 60. Processor 60 may receive the bioelectrical brain signal at any suitable time. In some examples, processor 60 receives the bioelectrical brain signal sensed by sensing module 66 at randomly or pseudo-randomly selected times or at predetermined intervals, while in other examples, processor 60 receives the bioelectrical brain signal sensed by sensing module 66 substantially continuously. The frequency with which processor 60 receives the bioelectrical brain signal sensed by sensing module 66 may be selected by a clinician in some examples.

While some portions of the disclosure generally refer to processor 60 (or another processor) receiving a bioelectrical brain signal, this may indicate that processor 60 (or another processor) receives information representative of the bioelectrical brain signal. The information representative of the bioelectrical brain signal may be, for example, a raw bioelectrical brain signal sensed by sensing module 66 of IMD 16 (or another sensing module), a parameterized bioelectrical brain signal generated by sensing module 66 or data generated based on the raw bioelectrical brain signal, such as one or more signal characteristics extracted from the sensed bioelectrical brain signal.

In addition or instead of automatically receiving sensed bioelectrical brain signals from sensor 66, in some examples, processor 60 is configured to receive the bioelectrical brain signal sensed by sensing module 66 in response to user input initiating a bioelectrical brain signal sensing. Processor 60 may receive the user input, for example, via IMD 16 or via programmer 14.

In the technique shown in FIG. 4, processor 60 of IMD 16 determines whether the sensed bioelectrical brain signal includes a biomarker (102). Example biomarkers are described above with respect to FIG. 2. As discussed above, the biomarker can indicate specific activity of a bioelectrical brain signal of patient 12 in one or more frequency sub-bands of a frequency band of interest and associated with a patient state, such as a power level in one or more frequency sub-bands or a spectral pattern of a bioelectrical brain signal in a frequency band of interest.

Processor 60 may employ one or more suitable signal processing techniques to determine whether a sensed bioelectrical brain signal has a biomarker indicative of a change in efficacy of electrical stimulation therapy delivered by IMD 16. In some examples, in order to determine whether a sensed bioelectrical brain signal includes the biomarker, processor 60 determine one or more frequency band (spectral) characteristics of a sensed bioelectrical brain signal and determine the sensed bioelectrical brain signal includes the biomarker in response to determining the one or more frequency band characteristics meet a particular set of criteria (e.g., a particular spectral pattern) associated with the biomarker.

In some examples, processor 60 substantially continuously receives (e.g., continuously receives or nearly continuously receives) the bioelectrical brain signal sensed by sensing module 66, but only samples the bioelectrical brain signal and determines whether the sampled bioelectrical brain signal includes a biomarker (102) at predetermined intervals, random (or pseudo-random) intervals, in response to user input, or any combination thereof (e.g., as described above with respect to receiving the bioelectrical brain signal). The frequency with which processor 60 samples the sensed bioelectrical brain signal or determines whether the sensed bioelectrical brain signal includes a biomarker may be selected by a clinician in some examples.

In response to determining the sensed bioelectrical brain signal includes a biomarker, processor 60 may detect a patient state and take a responsive action (104). In some examples, the responsive action includes generating an indication of the determined patient state. Processor 60 may store the indication in memory 62 of IMD 16, memory 82 of programmer 14, or a memory of another device. In some examples, processor 60 generates the indication by at least transmitting a notification to a user, such as patient 12 or a patient caretaker, e.g., via user interface 86 (FIG. 3) of programmer 14.

Processor 60 may be configured to provide a notification using any suitable technique. In some examples, processor 60 may be configured to control programmer 14 to display a visible message, emit an audible alert signal or provide a somatosensory alert (e.g., by causing a housing of programmer 14 to vibrate in a particular pattern or to vibrate continuously for a period of time) via user interface 86 in order to provide the notification, or any combination of the aforementioned types of notifications. In addition to or instead of the notifications provided via programmer 14, the notifications may be provided via another external device or via IMD 16. For example, processor 60 may cause outer housing 34 (FIG. 1) of IMD 16 to provide a somatosensory alert (e.g., by causing housing 34 of IMD 16 to vibrate in a particular pattern or to just vibrate continuously for a period of time) in order to provide the notification.

In other examples, processor 60 may be configured to provide a notification by sending a signal, via telemetry module 70, to a remote device, from which a clinician or another user may receive the notification. The remote device may be communicatively linked to IMD 16 (or programmer 14) using any suitable system. An example of suitable system includes the CareLink Network, available from Medtronic, Inc. of Minneapolis, Minn., which may include an external device, such as a server, and one or more computing devices that are coupled to IMD 16 and programmer 14 via a network.

Another example of a responsive action that processor 60 may take in response to determining the bioelectrical brain signal includes the biomarker associated with a particular patient state includes controlling therapy delivery to the patient based on the determined patient state. In some examples, if the patient state indicates the occurrence of a patient symptom or another state in which therapy delivery is desirable, then processor 60 controls stimulation generator 64 (FIG. 2) to initiate the delivery of electrical stimulation therapy to patient 12 in response to determining the bioelectrical brain signal includes the biomarker, and, therefore, in response to detecting the patient state. Other types of therapy in addition to, or instead of, electrical stimulation therapy are also contemplated.

In another example, if the patient state indicates the occurrence of a patient symptom or another state in which therapy delivery is desirable, processor 60 may modify one or more stimulation parameter values (or other therapy parameter values in the case of therapy other than electrical stimulation therapy) with which stimulation generator 64 (FIG. 2) generates electrical stimulation therapy in response to determining the bioelectrical brain signal includes the biomarker, and, therefore, in response to detecting the patient state. For example, processor 60 may determine that the detection of the patient state indicates the current therapy parameter values implemented by stimulation generator 64 are not effective or could be more effective in managing the patient's condition.

In some examples, the biomarker is associated with a movement state. If patient 12 is afflicted with a movement disorder or other neurodegenerative impairment, then therapy delivery, such as delivery of electrical stimulation therapy, a fluid delivery therapy (e.g., delivery of a pharmaceutical agent), fluid suspension delivery, or delivery of an external cue may improve the performance of motor tasks by patient 12 that may otherwise be difficult. These tasks may include at least one of initiating movement, maintaining movement, grasping and moving objects, improving gait associated with narrow turns, and so forth. By determining when patient 12 is in a movement state, e.g., using the technique shown in FIG. 4, therapy system 10 may provide "on demand" therapy to help manage symptoms of the patient's movement disorder.

In some examples, the biomarker is associated with a sleep state. In some cases, a patient condition, such as Parkinson's disease, may affect the quality of a patient's sleep. For example, when patient 12 attempts to sleep, patient 12 may successfully initiate sleep, but may not be able to maintain a certain sleep state (e.g., a nonrapid eye movement (NREM) sleep state). As another example, when patient 12 attempts to sleep, patient 12 may not be able to initiate sleep or may not be able to initiate a certain sleep state. For example, neurological disorders may cause patient 12 to have difficulty falling asleep and/or may disturb the patient's sleep, e.g., cause patient 12 to wake periodically. Further, neurological disorders may cause the patient to have difficulty achieving deeper sleep states, such as one or more of the NREM sleep states.

Some patients that are also afflicted with a movement disorder suffer from sleep disturbances, such as daytime somnolence, insomnia, disturbances in rapid eye movement (REM) sleep. For example, epilepsy is an example of a neurological disorder that may affect sleep quality. Other neurological disorders that may negatively affect patient sleep quality include movement disorders, such as tremor, Parkinson's disease, multiple sclerosis, or spasticity. The uncontrolled movements associated with such movement disorders may cause a patient to have difficulty falling asleep, disturb the patient's sleep, or cause the patient to have difficulty achieving deeper sleep states. Further, in some cases, poor sleep quality may increase the frequency or intensity of symptoms experienced by patient 12 due to a neurological disorder. For example, poor sleep quality has been linked to increased movement disorder symptoms in movement disorder patients.

Automatically delivering therapy to patient 12 in response to detecting the sleep state by at least detecting the biomarker associated with the sleep state may help alleviate at least some sleep disturbances. For example, in some examples, therapy system 10 may deliver stimulation to certain regions of brain 28 (FIG. 1), such as the locus coeruleus, dorsal raphe nucleus, posterior hypothalamus, reticularis pontis oralis nucleus, nucleus reticularis pontis caudalis, or the basal forebrain, during a sleep state in order to help patient 12 fall asleep, maintain the sleep state or maintain deeper sleep states (e.g., REM sleep). In addition to or instead of electrical stimulation therapy, a suitable pharmaceutical agent, such as acetylcholine, dopamine, epinephrine, norepinephrine, serotonine, inhibitors of noradrenaline or any agent for affecting a sleep disorder or combinations thereof may be delivered to brain 28 of patient 12. By alleviating the patient's sleep disturbances, patient 12 may feel more rested, and, as a result, therapy system 10 may help improve the quality of patient's life.

In some examples, the biomarker is associated with a speech state. Some patients that are also afflicted with a movement disorder suffer from speech disorder, such as impaired laryngeal function or articulatory dysfunction. Similarly, in the speech state, patient 12 may successfully initiate speech, but may not be able to maintain the verbal fluency, e.g., may unintentionally stop speaking or may have difficulty speaking. As another example, in the speech state, patient 12 may attempt to initiate speech without success. For example, patients with Parkinson's disease may be afflicted with hypokinetic dysarthria, which is a general difficulty speaking. It is believed that hypokinetic dysarthria is caused by dysfunction in the pallidal-cortical and/or thalamocortical circuitries, which may result in rigidity and dyskinesia in the respiratory, phonatory, and/or articulatory musculature. Initiating or otherwise adjusting therapy delivery to patient 12 in response to detecting a speech state may help alleviate at least some symptoms of a speech disorder. For example, in some examples, IMD 16 may deliver stimulation to certain regions of brain 28, such as bilateral stimulation of the subthalamic nucleus or globus pallidus. In addition to or instead of electrical stimulation therapy, a suitable pharmaceutical agent may be delivered to brain 28 of patient 12 to help manage speech impairment.

In some examples, if the biomarker is associated with a patient state for which therapy delivery is not desirable, processor 60 may control stimulation generator 64 (FIG. 2) to terminate the delivery of electrical stimulation therapy to patient 12 in response to determining the bioelectrical brain signal includes the biomarker. This responsive action may be taken if, for example, processor 60 controls stimulation generator 64 to deliver therapy to patient 12 until a patient state in which no symptoms or an otherwise positive patient state is achieved.

In addition or instead of the responsive actions discussed above, processor 60 may generate a patient diagnosis based on the determined patient state. For example, if patient 12 has been diagnosed with a patient condition and processor 60 detects a particular patient state associated with a sub-type of the patient condition, processor 60 may generate an indication of the patient condition sub-type in response to determining the bioelectrical brain signal includes the biomarker. In some examples, processor 60 may provide an indication of the patient diagnosis by, for example, transmitting a signal to programmer 14 via the respective telemetry modules 70, 84, and processor 80 of programmer 14 may control a display of user interface 86 to display the patient diagnosis.

In response to determining the sensed bioelectrical brain signal does not include the biomarker ("NO" branch of block 102), processor 60 may continue monitoring sensed bioelectrical brain signals for biomarkers. For example, processor 60 may continue receiving a bioelectrical brain signal (e.g., information representative of the bioelectrical brain signal) (100) and determining whether the bioelectrical brain signal includes a biomarker (102). Processor 60 may continue receiving the bioelectrical brain signal (100) at any suitable frequency, which may be regular or irregular, or based on user input (e.g., initiated by patient, patient caretaker, or clinician input).

In some examples, in the technique shown in FIG. 4, processor 60 selects the frequency band of interest, the one or more sub-bands of the frequency band of interest, or both. Processor 60 may, for example, select the frequency band of interest and determine the one or more frequency sub-bands of the frequency band of interest that are revealing of the patient state based on biomarker information 76 stored by memory 62 (FIG. 2).

As discussed above, different frequency bands of a bioelectrical brain signal are associated with different brain activity of the patient. For example, pathological synchronizations in beta band or other frequency bands of LFPs recorded from electrodes implanted in the basal ganglia of patients diagnosed with Parkinson's disease may be a biomarker of Parkinson's disease. For example, activity in a gamma band (e.g., about 35 Hz to about 100 Hz) may indicate the movement state of a patient or the sleep-wake state of a patient. As another example, as shown by the spectrogram illustrated in FIG. 5, the activity in a beta frequency band (e.g., about 13 Hz to about 35 Hz) in patients diagnosed with Parkinson's disease may vary as a function of the medicated state of the patient. For example, the power level in the beta band may decrease when the patient is under the influence of medication.

Figure 5:
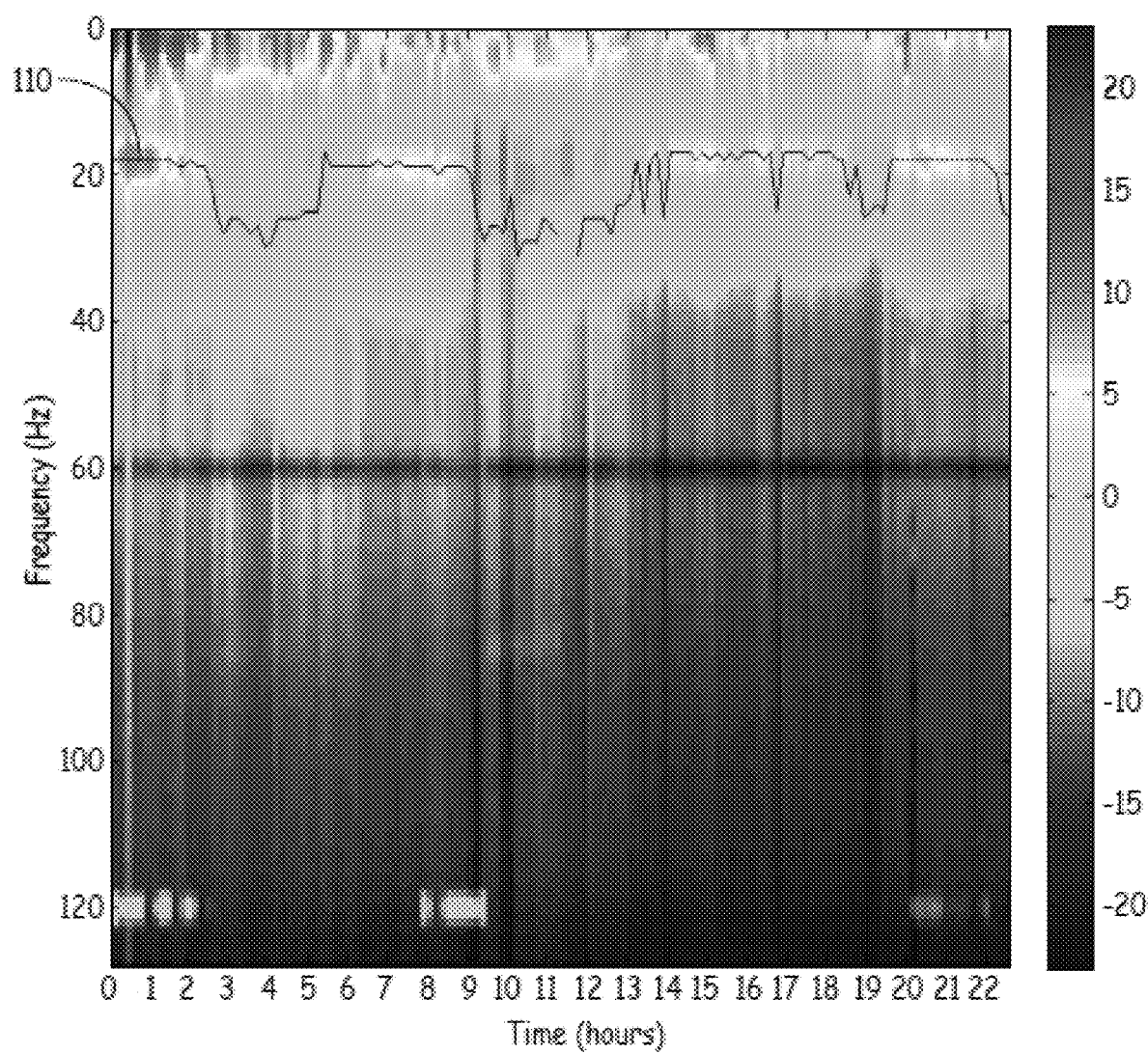
FIG. 5 is an example spectrogram of a bioelectrical brain signal sensed within a brain of a human subject.

FIG. 5 is an example spectrogram of a bioelectrical brain signal sensed within a brain of a human subject. In particular, the bioelectrical brain signal is a LFP recorded from electrodes implanted in a brain of a patient diagnosed with Parkinson's disease. The graph shown in FIG. 5 illustrates the power spectra of the LFPs over approximately 24 hours and illustrates how much of the sensed bioelectrical brain signal lies within each given frequency band over a range of frequencies. The length of the LFP recording shown in FIG. 5 permits the therapeutic effects of a medication taken by the human subject medication) to be observed. The y-axis of the spectrogram indicates the frequency of the bioelectrical brain signal, the x-axis indicates time, and the z-axis, which extends substantially perpendicular to the plane of the image of FIG. 5, as indicated by the color of the spectrogram, indicates a power level of the bioelectrical brain signal. The spectrogram provides a three-dimensional plot of the signal strength of the frequency content of a bioelectrical brain signal as it changes over time.

The spectrogram shown in FIG. 5 indicates that high energy activity is observed in the beta frequency band (e.g., about 13 Hz to about 35 Hz in the example shown in FIG. 5) with varying amplitudes (as indicated by the color key shown on the far right side of the spectrogram) depending on the medication state (e.g., on medication or off medication) of the patient. FIG. 5 depicts a line graph 110 that indicates the fluctuation of the amplitude of the LFPs in a frequency sub-band (e.g., about 18 Hz to about 28 Hz) of the beta frequency band. The spectrogram shown in FIG. 5 indicates that the amplitude (also referred to herein as the "power level" or "activity") in at least one frequency sub-band (e.g., about 18 Hz to about 28 Hz) of the beta frequency band may fluctuate as a function of the medication state of a patient. As a result, one or more spectral characteristics (e.g., a spectral pattern) of the LFP in a particular beta frequency sub-band of the beta frequency band may indicate a patient state in which therapeutic effects of medication are observed.

Figure 6A:
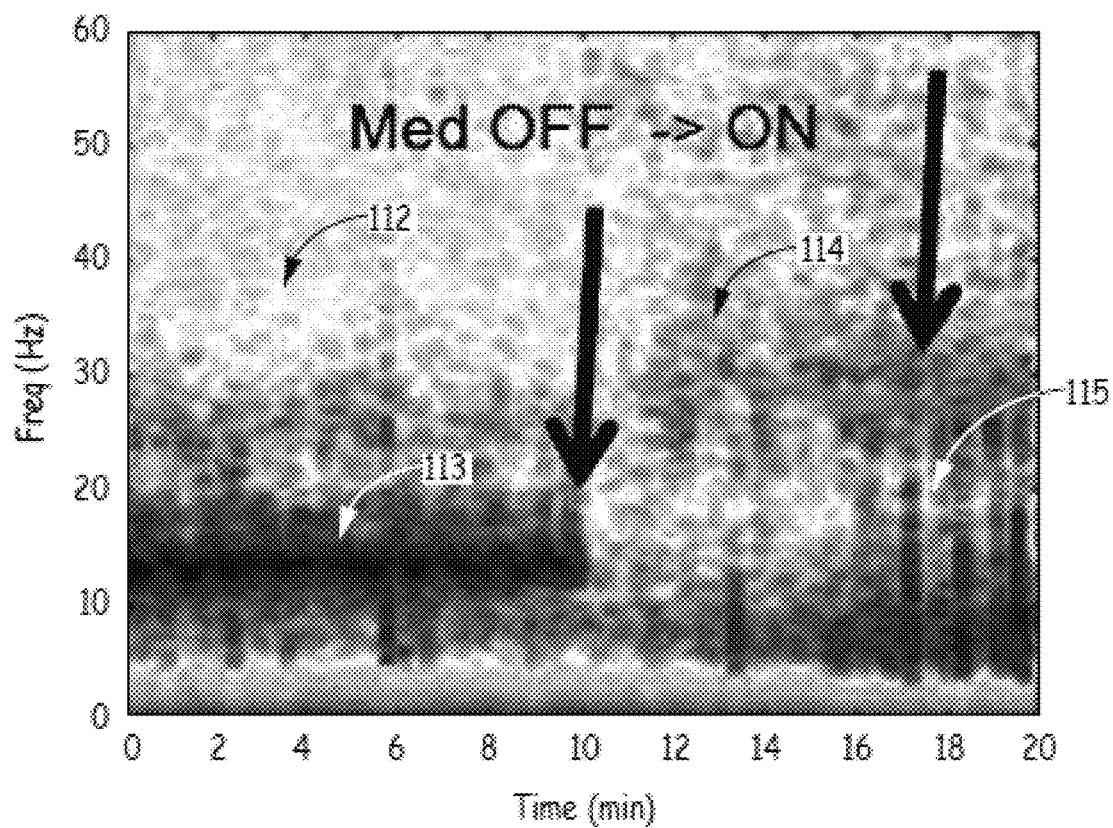
FIGS. 6A and 6B are example spectrograms of bioelectrical brain signals sensed within brains of human subjects, and illustrate the effects of medication on activity of the bioelectrical brain signals.
Figure 6B:
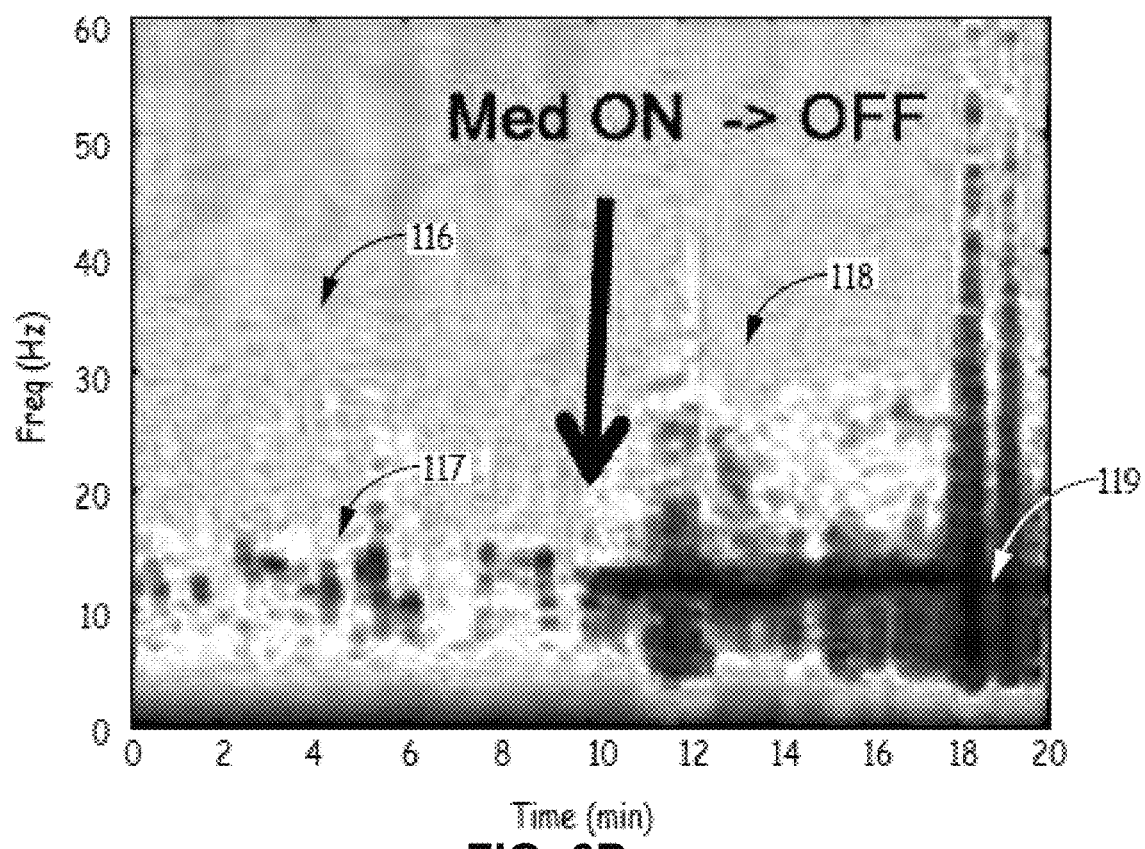

FIGS. 6A and 6B are example spectrograms of a bioelectrical brain signal sensed within a brain of a human subject and illustrate the effects of medication on activity in a beta frequency band (e.g., about 13 Hz to about 35 Hz) in a human subject diagnosed with Parkinson's disease. The sensed bioelectrical brain signal is a LFP recorded from electrodes implanted in a brain of a patient diagnosed with Parkinson's disease. As with the spectrogram shown in FIG. 5, the y-axes of the spectrograms shown in FIGS. 6A and 6B indicate the frequency band of the bioelectrical brain signal, the x-axes indicates time, and the z-axes, which extend substantially perpendicular to the plane of the respective image, as indicated by the color of the spectrogram, indicate a power level of the bioelectrical brain signal.

In FIG. 6A, during a first time period 112, the human subject is in a pathological state and is not under the influence of therapy to mitigate effects of a movement disorder. As shown in FIG. 6A, in the first time period 112, a power level of the bioelectrical brain signal of the human subject in a first frequency sub-band (e.g., about 13 Hz to about 20 Hz) of the beta frequency band (e.g., about 13 Hz to about 35 Hz) is relatively high, as indicated by the relatively intense color 113 in FIG. 6A. In particular, during time period 112, the peak activity in the beta band occurs in the first frequency sub-band. In a second time period 114, the human subject is under the influence of medication (e.g., a pharmaceutical agent) to mitigate effects of the movement disorder. As shown in FIG. 6A, compared to the first time period 112, the beta band activity in the first frequency sub-band decreases during the second time period 114 in which the human subject is receiving movement disorder therapy and beta band activity in a second frequency sub-band (e.g., about 20 Hz to about 30 Hz) of the beta band increases. In particular, during time period 114, the peak activity in the beta band 115 occurs in the second frequency sub-band, which is different than the first frequency sub-band and does not overlap with the first frequency sub-band.

The spectrogram shown in FIG. 6A demonstrates that even though the power level in the overall beta band (e.g., about 13 Hz to about 35 Hz) may not change significantly, if at all, before and after the onset of the effects of the medication, the distribution of power between different sub-bands of the beta band may shift in response to the receipt of therapy to manage the movement disorder symptoms. This change in the activity levels in the frequency sub-bands may not be observed if the activity in the beta band is just observed.

The test results shown in FIG. 6A indicates that a shift in peak power within the beta band between the first and second frequency sub-bands of the beta band may be a biomarker for a positive response to medication. It is believed that the shift in peak power of a frequency band of interest between two or more sub-bands of the frequency band of interest may be a biomarker for other patient states instead of or in addition to the state in which a positive response to medication is observed, such as, but not limited to, a movement state, a sleep state, a speech state, a state in which one or more symptoms of a patient condition are observed, and the like.

In FIG. 6B, during a first time period 116, the human subject is in a pathological state and is not under the influence of therapy to mitigate effects of a movement disorder. As shown in FIG. 6B, in the first time period 116, the dominant beta band activity in a first frequency sub-band (e.g., about 13 Hz to about 20 Hz) of the beta frequency band (e.g., about 13 Hz to about 35 Hz) is relatively high, as indicated by the relatively intense color 117 in FIG. 6B. In particular, during time period 116, the peak activity in the beta band occurs in the first frequency sub-band. In a second time period 118, the human subject is under the influence of medication (e.g., a pharmaceutical agent) to mitigate effects of the movement disorder. As shown in FIG. 6B, compared to the first time period 116, the dominant beta band activity is in a broader frequency sub-band during the second time period 118 in which the human subject is receiving movement disorder therapy. In particular, during time period 118, the dominant activity 119 in the beta band occurs in a second frequency sub-band spanning from about 13 Hz to about 35 Hz, which is different than the first frequency sub-band, but overlaps with the first frequency sub-band.

The spectrogram shown in FIG. 6B demonstrates that even though the power level in the beta band may not change significantly, if at all, before and after the onset of the effects of the medication, the width of the sub-bands of the beta band that exhibit a relatively highest level of activity may change in response to the receipt of therapy to manage the movement disorder symptoms. Again, this change in the activity levels in the frequency sub-bands may not be observed if the activity in just the overall the beta band is observed.

The test results shown in FIG. 6B indicate that a change in the width of a frequency sub-band of the beta band that includes a relatively highest level of activity may be a biomarker for a positive response to medication. It is believed that a change in the width of a frequency sub-band of the beta band that includes a relatively highest level of activity may be a biomarker for other patient states instead of or in addition to the state in which a positive response to medication is observed, such as, but not limited to, a movement state, a sleep state, a speech state, a state in which one or more symptoms of a patient condition are observed, and the like.

The test results shown in FIGS. 6A and 6B indicate that a shift in peak power between the first and second frequency sub-bands of the beta band may be a biomarker for a positive response to medication. The peak power can be indicated by the power level at one frequency or the average power level for a plurality of frequencies (e.g., a frequency sub-band). It is believed that the shift in peak power between two or more sub-bands of a frequency band of interest may be biomarker for other patient states instead of or in addition to the state in which a positive response to medication is observed (e.g., a movement state, a sleep state, a speech state, a state in which one or more symptoms of a patient condition are observed, or the like).

It is believed that for some patients, one or more of a frequency sub-band in which a peak power level (also referred to herein as a peak amplitude) is observed or a spectral pattern (also referred to as oscillatory activity) of a bioelectrical brain signal may be indicative of a particular patient state. The spectral pattern may be, for example, a morphology of a plot the power level versus frequency (e.g., a characteristic of a peak of the plot, such as width of the peak or the number of modes of the peak), or another pattern with which the power distribution between sub-bands of the frequency band shifts.

FIGS. 7A-7D illustrate different (spectral) patterns in oscillatory activity that may be indicative of particular patient states (e.g., the same patient state or different patient states, depending on the patient condition and the patient). In particular, FIGS. 7A-7D illustrate the power spectra of LFPs recorded from electrodes implanted in the brains of human subjects diagnosed with Parkinson's disease. The x-axis of each of the power spectra shown in FIGS. 7A-7D indicates the frequency of the bioelectrical brain signal, and the y-axis of each power spectra indicates the spectral amplitude (in units of microvolts ($\mu v$ ms)). The power (as indicated by the y-axis value) of the bioelectrical brain signal at a particular frequency (as indicated by the x-axis value) can be in units of microvolts squared ($\mu v^2$), or, as shown in FIG. 7, the root mean square of the microvolts squared value (referred to in FIGS. 7A-7D as $\mu v$ ms).

Figure 7A:
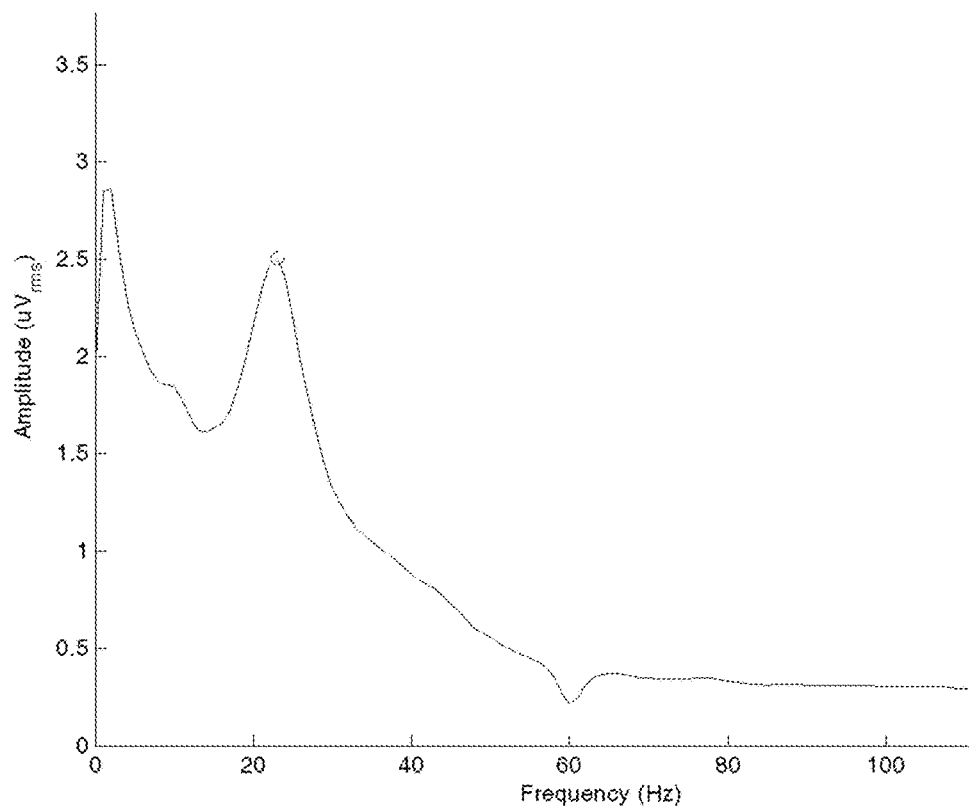
FIGS. 7A-7D illustrate the power spectra of local field potentials (LFPs) recorded from electrodes implanted in brains of human subjects diagnosed with Parkinson's disease.
Figure 7B:
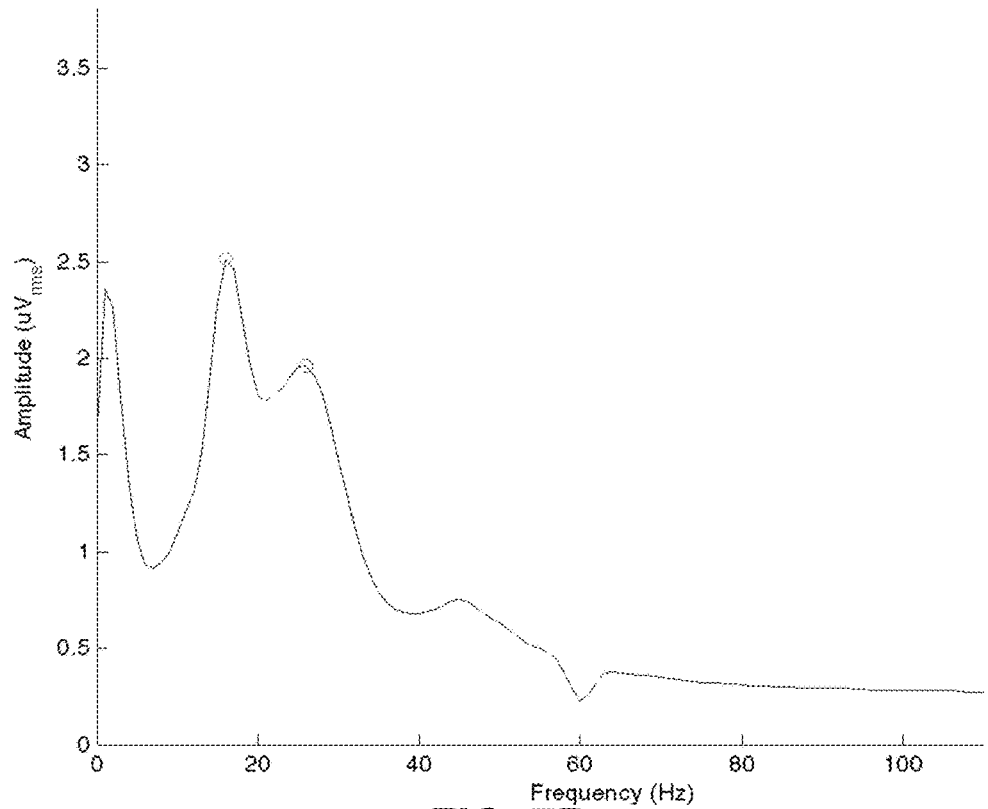
Figure 7C:
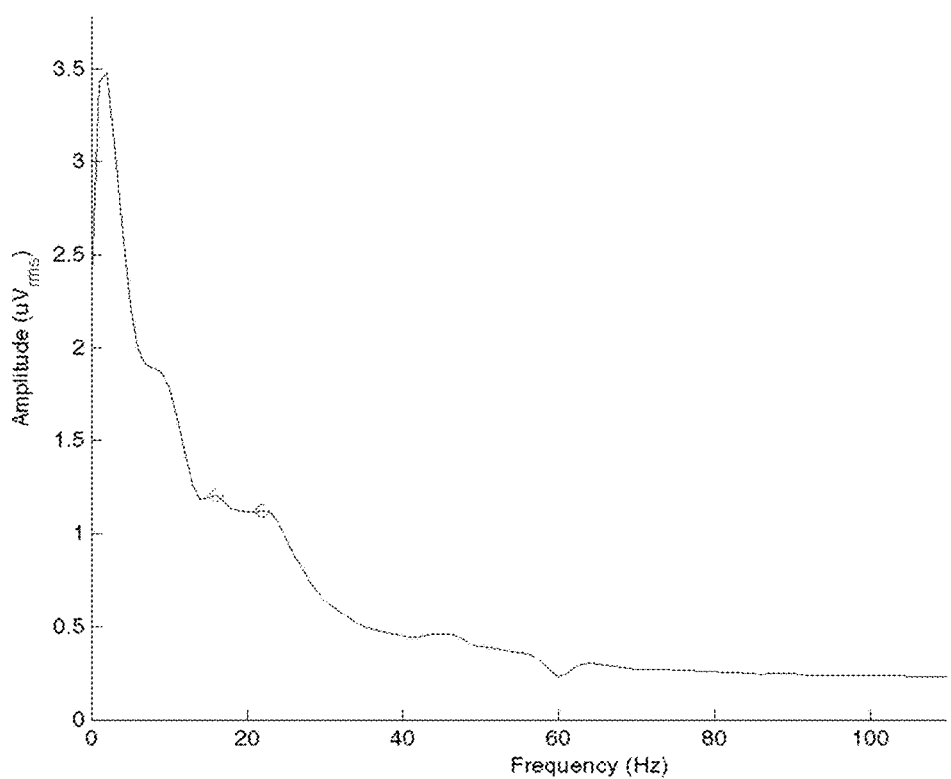
Figure 7D:
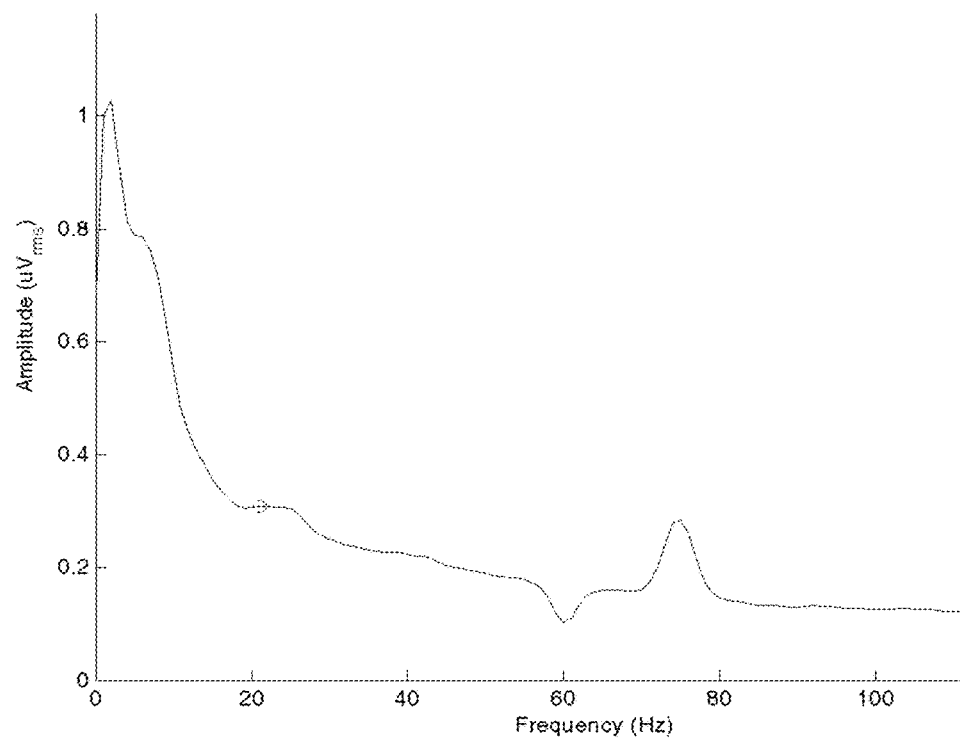

FIGS. 7A-7D illustrate frequency-domain graphs of sensed bioelectrical brain signals having different signal strength distributions. FIG. 7A illustrates a LFP exhibiting a single signal peak amplitude (also referred to as a "unimodal" peak) in the beta band, where the peak power level occurs in a particular a frequency sub-band of the beta band. FIG. 7B illustrates a LFP exhibiting a multiple signal peak amplitudes (also referred to as a "bimodal" or "multimodal" peak) in the beta band, where the peak power levels are in different frequency sub-bands of the beta band. In other examples, a bimodal peak indicative of a particular patient state can include two different peak power levels within different frequency bands in the power spectrum. FIG. 7C illustrates a LFP exhibiting an elevated plateau in a frequency sub-band of the beta band without a clear peak. An elevated plateau may be indicated by, for example, the power level staying substantially flat or at least not exhibiting a non-exponential fall-off within a particular frequency sub-band, across two or more sub-bands of a frequency band of interest, or even across two or more frequency bands of interest instead of decreasing exponentially. FIG. 7D illustrates a LFP exhibiting a peak power level in the gamma band.

It is believed that, in some cases, the different morphologies shown in FIGS. 7A-7D may be associated with different patient states. The different morphologies may be characterized by a predetermined characteristic of a signal strength distribution, such as, but not limited to, one or more of a peak width less than or equal to a first threshold value, a peak width greater than or equal to a second threshold value, a unimodal peak, or a bimodal peak. In addition, in some examples, a particular morphology indicative of a patient state and stored by IMD 16 as a biomarker can be a particular difference (e.g., difference in power level) in morphology relative to a baseline bioelectrical brain signal.

Short term recordings of LFPs may not provide sufficient data to compare the activity of the different frequency sub-bands within the beta band (or gamma band or another frequency band of interest, which may vary depending on the patient condition) to determine how these different spectral patterns of LFPs (or other bioelectrical brain signals) may indicate a particular patient state.

Based on longer duration recordings (e.g., on the order of hours or even days, such as 24 hours) of LFPs, it is believed that not only is the power level in a particular frequency band (e.g., the beta band or the gamma band) of a sensed bioelectrical brain signal indicative of a patient state, but other spectral characteristics (e.g., indicative of activity of a bioelectrical brain signal of a patient in one or more frequency sub-bands of a frequency band of interest) may be indicative of a patient state and, in some cases, a more specific patient state than the power level in the broader frequency band. The longer duration recordings may, for example, provide a better understanding of the spectral and temporal characteristics of the LFP signals while patents undergo symptom testing both with and without medication or other therapy. The other spectral characteristics that may be indicative of a patient state include, for example, the power level of a bioelectrical brain signal of the patient in one or more frequency sub-bands of the frequency band, a shift in a power distribution (e.g., a peak power or an average power over a particular range of frequencies) between sub-bands of the frequency band, a change in the peak frequency within one or more frequency sub-bands, a characteristic of a distribution of a signal strength within a frequency band (e.g., a narrow peak, a broad peak, a unimodal peak, or a bimodal peak), or a width or a variability (e.g., in the width), or the one or more frequency sub-bands exhibiting a relatively high or low level of activity.

Figure 8A:
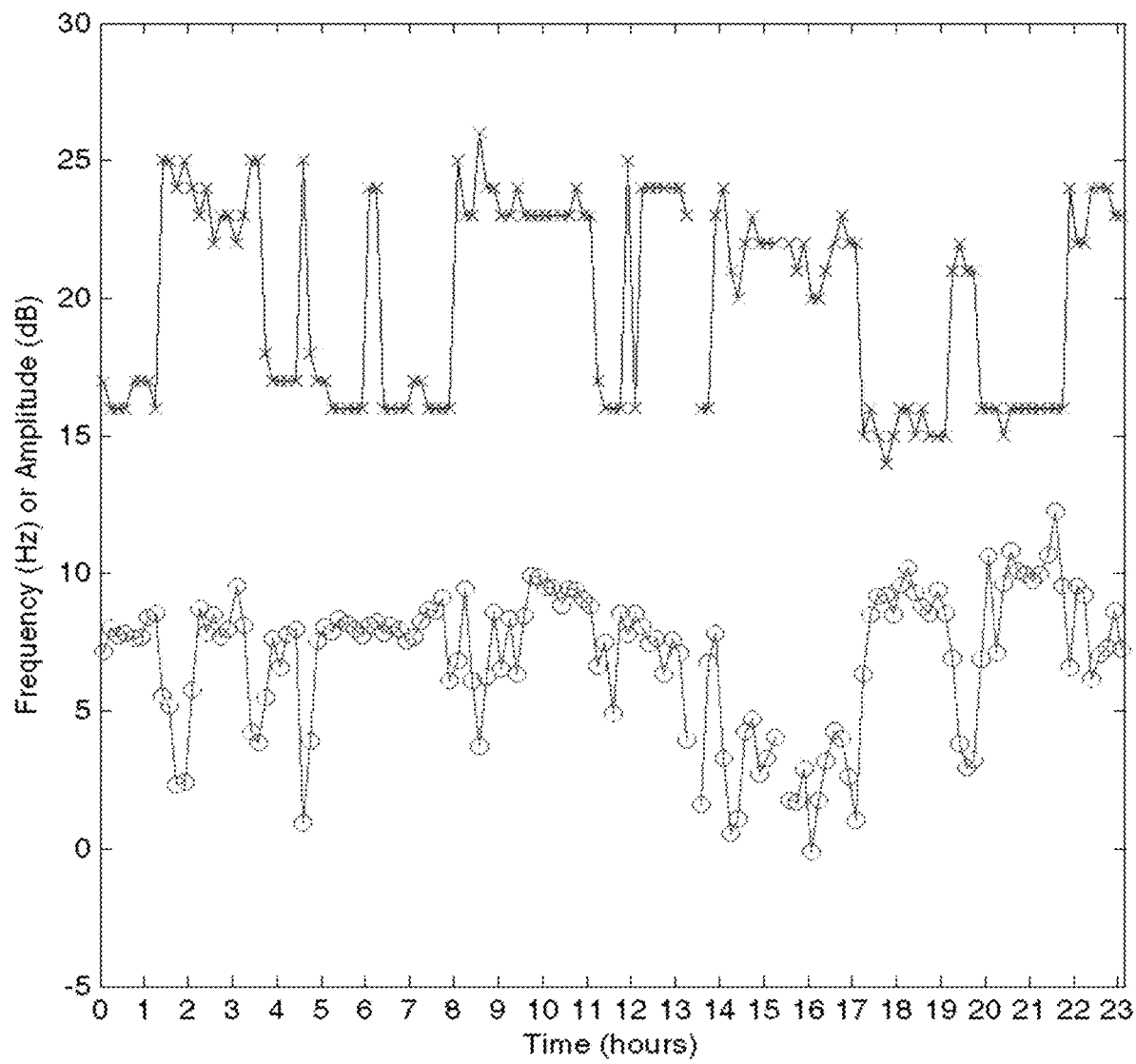
FIG. 8A is a graph that illustrates characteristics of the beta band activity of a LFP sensed within a basal ganglia of a brain of a human patient over an approximately 24 hour period of time, and, in particular, illustrates the peak spectral amplitude of the beta band activity and the corresponding frequency at which the peak spectral amplitude occurred.
Figure 8B:
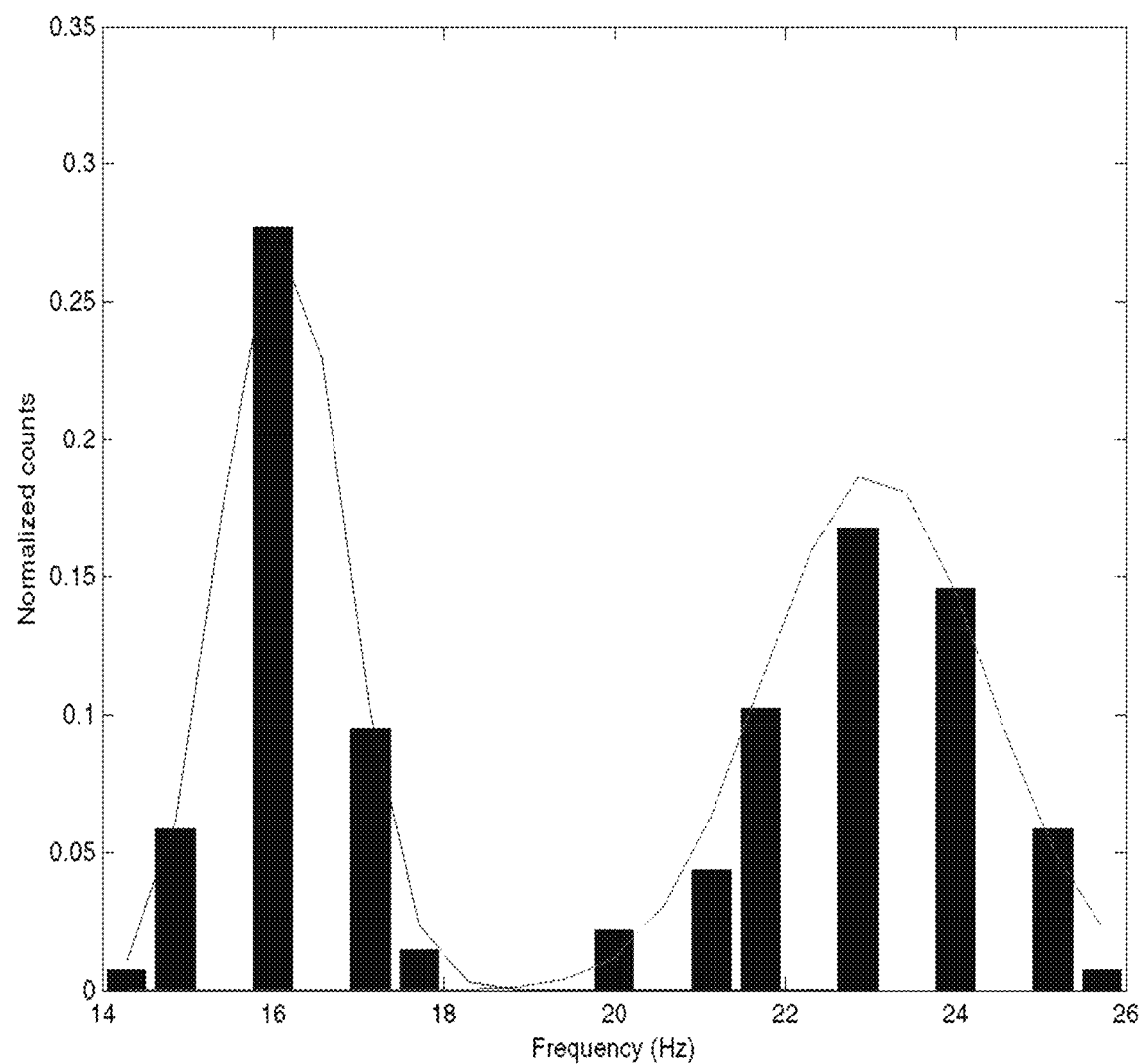
FIG. 8B illustrates a histogram of the beta band frequencies shown in FIG. 8A corresponding to the peak spectral amplitudes.

FIGS. 8A and 8B illustrate characteristics of the beta activity of LFPs sensed within a basal ganglia of a brain of a human patient over an approximately 24 hour period of time. The test results that shown in FIGS. 8A and 8B indicate that, in addition to the changes of LFP amplitude (power level), the LFP spectral patterns may also change as a function of the patient state. In particular, FIG. 8A illustrates the peak amplitude (as represented by circles along the bottom plot) of the beta band activity and the corresponding frequency (as represented by the crosses along the top plot) at which the peak amplitude occurred. FIG. 8B illustrates a histogram of the beta band frequencies corresponding to the peaks. The histogram indicates there was a bimodal distribution of the beta band frequencies corresponding to the peak amplitudes of the sensed LFPs. The probability density functions of two normal distributions are overlaid in FIG. 8B so that two distinct beta frequency bands can be identified.

The data analysis shown in FIGS. 8A and 8B indicate that the beta frequency band activities in different frequency sub-bands of the beta band (e.g., a low beta sub-band having a frequency range of about 13 Hz to about 20 Hz and a high beta sub-band having a frequency range of about 20 Hz to about 30 Hz) may be associated with different components of the Parkinson's disease symptoms. This indicates that activity of a bioelectrical brain signal of a patient in one or more frequency sub-bands of a frequency band of interest, rather than activity in the broader frequency band itself, may be used to determine a patient state. The frequency sub-bands of interest (e.g., the sub-bands bands that correspond to normal and pathological brain behaviors, the sub-bands bands that indicate a patient response medications or other therapies), the power level in a particular frequency sub-band, or another spectral characteristic of a bioelectrical brain signal indicative of a particular patient state may be determined based on relatively long term bioelectrical brain signal recordings from a patient.

The data analysis shown in FIGS. 8A and 8B also indicates that the high and low beta in the case of bimodal peaks may respond different to brain states as well as to therapies, such that one or more characteristics of the bimodal peak may be indicative of a patient state. The characteristics of the bimodal peak can include, for example the frequency sub-band in which the high beta activity is observed and the frequency sub-band in which the low beta activity is observed, the frequency difference between these sub-bands, the power level of the high beta activity, the power level of the low beta activity, the ratio of the power levels of the high and low beta activities, the difference in the power levels of the high and low beta activities, and the like.

Figure 9:
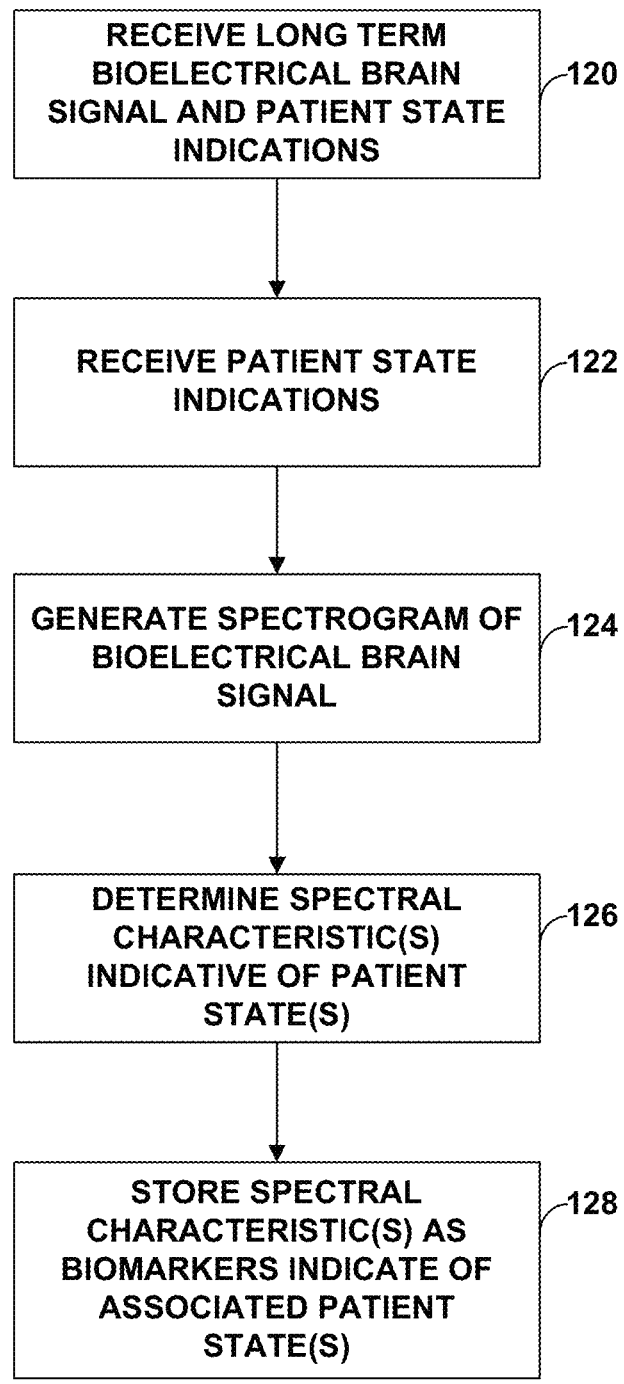
FIG. 9 is a flow diagram illustrating an example technique for determining one or more biomarkers indicative of a particular patient state.

As indicated above, one or more spectral characteristics of a bioelectrical brain signal sensed within particular structures of brain 28 of patient 12 and indicative of particular patient states may be stored as a biomarker indicative of a particular patient state. In some examples, the biomarkers may be determined during a learning phase. One example technique that may be implemented during a learning phase to determine one or more biomarkers indicative of a particular patient state is shown in FIG. 9. While the technique shown in FIG. 9, as well as some other figures are described with respect to processor 80 of programmer 14, in other examples, a processor of another device, such as processor 60 of IMD 16 (FIG. 2) can perform any part of the techniques described herein, alone or in combination with another device.

In accordance with the technique shown in FIG. 9, processor 80 of programmer 14 receives a long term bioelectrical brain signal recording, which indicates a bioelectrical brain signal recorded by sensing module 66 (FIG. 2) of IMD 16 (120). The length of the bioelectrical brain signal recording is selected such that the bioelectrical signal sensed by sensing module 66 during at least two different patient states is recorded. Processor 80 may receive the long term bioelectrical brain signal recording (120) from IMD 16 or from another device, such as a storage device.

In addition, processor 80 receives patient state indications that indicate the occurrence of a particular patient state (122). The patient state indications correlate in time with the bioelectrical brain signal recording, such that processor 80 receives both the bioelectrical brain signal sensed while the patient state was observed and an indication of the patient state. Processor 80 can receive the indication of the patient state via any suitable technique, such as based on input from patient 12, a patient caretaker, or another person, or based on input from another sensor (e.g., an accelerometer or another type of motion sensor may indicate a movement state). In some examples, patient 12 (or another user) may interact with user interface 86 of programmer 14 (FIG. 3) to provide the input. In other examples, patient 12 (or another user) may provide the input by directly interacting with IMD 16. For example, a motion sensor (e.g., an accelerometer, pressure transducer, gyroscope, or piezoelectric crystal) integrated into or on housing 34 of IMD 16 may be configured to generate a signal that is indicative of patient 12 tapping IMD 14 through the skin. The number, rate, or pattern of taps may be associated with different patient states, and processor 80 may identify the tapping by patient 12 to determine when patient input is received and what type of patient state is indicated by the patient input.

In the technique shown in FIG. 9, processor 80 generates a spectrogram of the bioelectrical brain signal (124) and determines one or more spectral characteristics indicative of one or more patient states (126). For example, processor 80 may determine (e.g., select) one or more frequency sub-bands of a frequency band of interest, and determine, automatically or with the aid of a clinician, one or more spectral characteristics of the frequency sub-bands of the frequency domain of the bioelectrical brain signal that are correlated with the patient state indication. The characteristic of the frequency sub-band can be, for example, a characteristic that exhibited a change within a particular time range (e.g., less than about 5 seconds) prior to or after the patient state indication. In the example shown in FIG. 9, the one or more spectral characteristics determined by processor 80 are stored in memory 82 (or a memory of another device, such as IMD 16 or a remote server) as biomarkers indicative of the associated patient state (128).

Processor 80 may determine one or more frequency sub-bands and one or more frequency bands of interest using any suitable technique. For example, processor 80 may determine the frequency bands and sub-bands (which may be referred to as "functional bands" in some examples) of the frequency bands that exhibit activity changes within a particular time range of time relative to the time of the patient state indication. As another example, processor 80 may determine one or more frequency sub-bands and one or more frequency bands of interest based on user input received via user interface 86.

In some examples, after identifying specific frequency sub-bands of interest, processor 80 may generate a histogram based on the power spectra (e.g., as part of a power spectral analysis) to analyze the relative frequency distribution of power in the frequency sub-bands and determine patient state biomarkers based on the frequency distribution. In addition, in some examples, processor 80 may perform a coherence analysis to cross-compare different biomarkers, and perform a correlation analysis to determine the relationship between these biomarkers and one or more patient states. In this way, processor 80 may use statistical measures to automatically determine one or more spectral characteristics of a bioelectrical brain signal with which a patient state may be automatically detected.

By tracking of a bioelectrical brain signal of patient 12 over relatively long periods of time (e.g., on the order of hours or even days), characteristics of the one or more frequency sub-band components indicative of one or more patient states may be observed. Using the technique shown in FIG. 9, processor 80 may perform a power spectral analysis of the sensed bioelectrical brain signal to determine one or more biomarkers (e.g., frequency sub-band components) indicative of one or more patient states.

The one or more biomarkers may facilitate clinical decisions regarding the patient condition (e.g., to assess the patient condition sub-type), delivery of treatment, such as the selection of a type of therapy (e.g., drug delivery or electrical stimulation therapy) or the selection of one or more efficacious therapy delivery parameter values. For example, processor 80, alone or with the aid of a clinician, can determine the effects of a particular type of therapy, such as a type of medication taken by patient 12, electrical stimulation therapy, drug delivery therapy, or any combination thereof, on spectral bands of a bioelectrical brain signal sensed in brain 28 of patient 12 by comparing the shifts in the location, amplitude, and width of signal peaks relative to a baseline state (e.g., in which no therapeutic effects of the therapy are observed).

In addition or instead, processor 60 of IMD 16, processor 80 of programmer 14 or another processor, alone or with the aid of a clinician, may use the one or more biomarkers to control therapy to maintain a threshold level of activity in one or more particular frequency sub-bands or, depending on the patient condition, to maintain a lack of activity in the one or more frequency sub-bands), or to achieve a particular change in the activity in the one or more frequency sub-bands. In this way, the biomarkers may be used by processor 60 of IMD 16 or another device to control closed-loop therapy.

In other examples of the technique shown in FIG. 9, processor 80 may present, via a display of user interface 86, information regarding the spectral components (e.g., frequency sub-bands of interest, spectral patterns, or both) of a sensed bioelectrical brain signal and a user (e.g., a clinician) may select one or more biomarkers based on the presented information.

Figure 10:
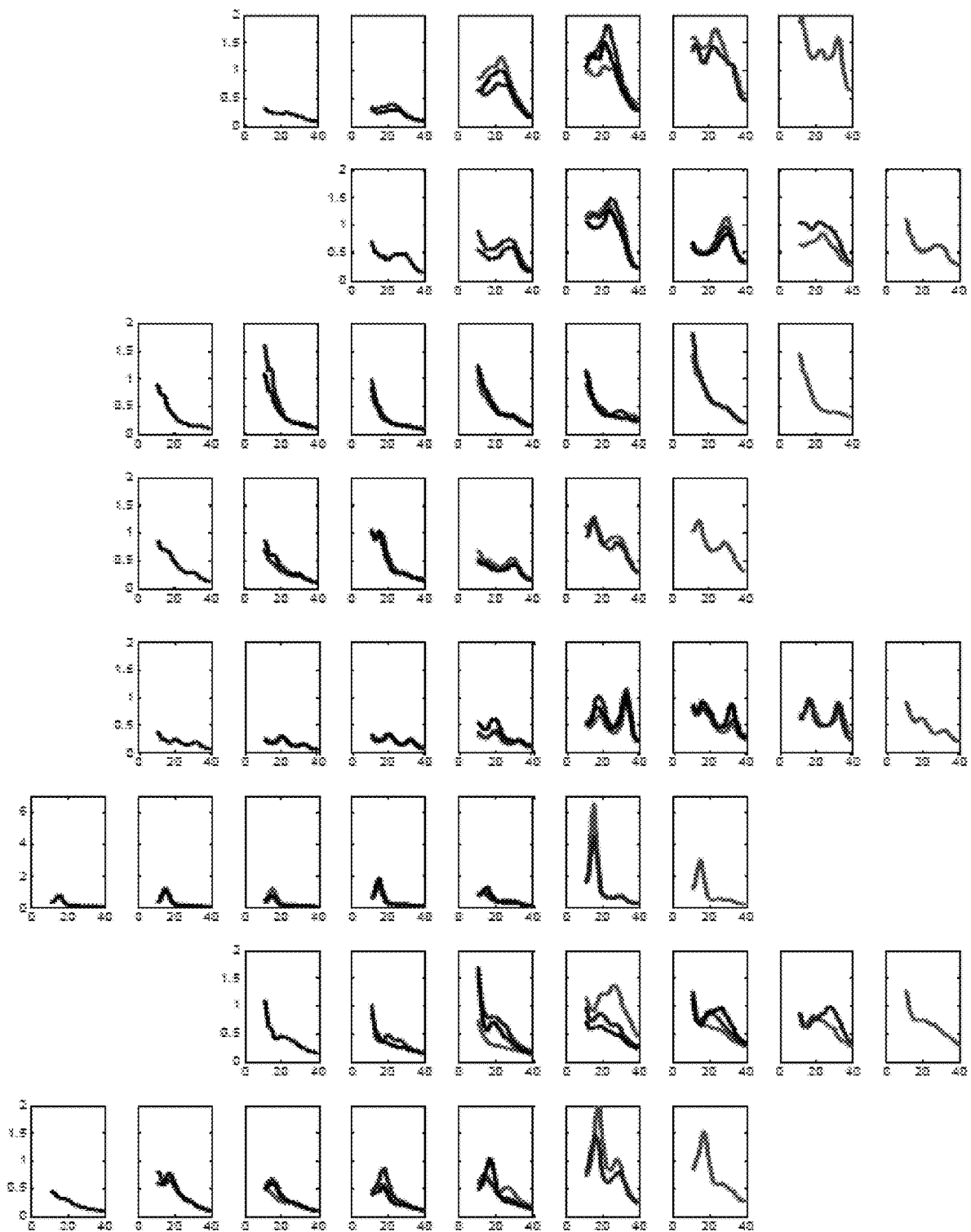
FIG. 10 illustrates a plurality of graphs that each indicates the beta band activity of a LFP sensed within brains of human subjects.

FIG. 10 illustrates a plurality of graphs that each indicates the beta band activity of a LFP sensed within a brain of a human subject diagnosed with Parkinson's disease. Graphs corresponding to one of five human subjects are shown in FIG. 10. The x-axis of each graph shown in FIG. 10 indicates the frequency of the LFP sensed within brains of human subjects and the y-axis indicates the spectral amplitude (also referred to herein as the "power level") of the activity in the particular frequency along the x-axis in units of microvolts squared ($\mu v^2$). Each row of graphs in FIG. 10 indicates the LFP sensed in one hemisphere of a brain of a human subject, with each graph indicating a different depth of electrodes. In each row, the graphs from left to right indicate a deeper location within the brain of the subject as the lead was moved in approximately two millimeter (mm) increments in a deep direction. For each subject, a LFP was sensed for a duration of about 60 seconds to about 90 seconds with implanted electrodes as the lead carrying the electrodes was implanted to deliver electrical stimulation to the subthalamic nucleus in the brain of the patient.

The data shown in FIG. 10 indicates that the spectral pattern of the LFP activity in a brain of a patient over time may depend on the depth within the brain of the sense electrodes with which the LFP is sensed. In addition, the graphs in FIG. 10 indicate that different patients exhibit different beta band activity within frequency sub-bands of the beta band, as indicated by different spectral patterns (e.g., different peak shapes). This may indicate, for example, that different subtypes of Parkinson's disease are associated with different characteristics of beta sub-band activity, such as different spectral patterns.

In some examples, programmer 14 or another device, such as IMD 16, is configured to determine whether a patient has a particular patient condition (e.g., Parkinson's disease) based on activity of a bioelectrical brain signal of a patient in one or more frequency sub-bands of a frequency band of interest. One or more frequency domain characteristics of a bioelectrical brain signal, such as the activity of a bioelectrical brain signal of a patient in one or more frequency sub-bands of a frequency band of interest, may be markers for the presence of absence of a particular patient condition. For example, bioelectrical brain signals of patients without a particular patient condition may not exhibit certain activity in one or more frequency sub-bands of a frequency band of interest, whereas bioelectrical brain signals of patients with the patient condition may exhibit certain activity in one or more frequency sub-bands of a frequency band of interest. As an example, bioelectrical brain signals of patients that do not have Parkinson's disease may not exhibit certain shifts in power levels between two or more frequency sub-bands of a frequency band of interest, whereas at least some patients with Parkinson's disease may exhibit the shifts. Thus, activity in one or more frequency sub-bands of a frequency band of interest may be indicative of the presence of the patient condition and may, therefore, be used in some examples to diagnose the patient condition.

The bioelectrical brain signals sensed to diagnose the patient condition or otherwise determine a patient state may be sensed via implanted electrodes or via external (e.g., scalp) electrodes.

While the techniques described above are primarily described as being performed by processor 60 of IMD 16 or processor 80 of programmer 14, in other examples, one or more other processors may perform any part of the techniques described herein alone or in addition to processor 60 or processor 80. Thus, reference to "a processor" may refer to "one or more processors." Likewise, "one or more processors" may refer to a single processor or multiple processors in different examples.

The techniques described in this disclosure, including those attributed to IMD 16, programmer 14, or various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as clinician or patient programmers, medical devices, or other devices.

In one or more examples, the functions described in this disclosure may be implemented in hardware, software, firmware, or any combination thereof. If implemented in software, the functions may be stored on, as one or more instructions or code, a computer-readable medium and executed by a hardware-based processing unit. Computer-readable media may include computer-readable storage media forming a tangible, non-transitory medium. Instructions may be executed by one or more processors, such as one or more DSPs, ASICs, FPGAs, general purpose microprocessors, or other equivalent integrated or discrete logic circuitry. Accordingly, the term "processor," as used herein may refer to one or more of any of the foregoing structure or any other structure suitable for implementation of the techniques described herein.

In addition, in some aspects, the functionality described herein may be provided within dedicated hardware and/or software modules. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components. Also, the techniques could be fully implemented in one or more circuits or logic elements. The techniques of this disclosure may be implemented in a wide variety of devices or apparatuses, including an IMD, an external programmer, a combination of an IMD and external programmer, an integrated circuit (IC) or a set of ICs, and/or discrete electrical circuitry, residing in an IMD and/or external programmer.

Various examples have been described. These and other examples are within the scope of the following claims.

What is claimed is:

1. A method comprising:
receiving, with one or more processors, a bioelectrical brain signal of a patient;
determining, with the one or more processors, the bioelectrical brain signal includes a biomarker indicative of a patient state, wherein determining the bioelectrical brain signal includes the biomarker comprises:
selecting a frequency band of interest of the bioelectrical brain signal from a plurality of predetermined frequency bands based on biomarker information stored by a memory, wherein the biomarker information comprises a plurality of biomarkers, each biomarker of the plurality of biomarkers comprising spectral characteristics of two or more frequency sub-bands of a particular frequency band of the plurality of predetermined frequency bands,
wherein the predetermined frequency bands include two or more of a delta band, a theta band, an alpha band, a beta band, a gamma band, or a high gamma band, and
wherein the frequency band of interest includes a plurality of frequency sub-bands;
after selecting the frequency band of interest, selecting two or more frequency sub-bands from the plurality of frequency sub-bands based on the biomarker information,
wherein each of the selected two or more frequency sub-bands is narrower than the frequency band of interest; and
controlling therapy delivery by a medical device to the patient based on determining the bioelectrical brain signal includes the biomarker.

2. The method of claim 1, wherein receiving the bioelectrical brain signal comprises receiving, with the one or more processors, the bioelectrical brain signal from a sensing module configured to sense the bioelectrical brain signal via one or more electrodes.

3. The method of claim 1, wherein determining the bioelectrical brain signal includes the biomarker comprises determining the bioelectrical brain signal includes the biomarker based on a spectral pattern of the bioelectrical brain signal in the selected two or more frequency sub-bands of the frequency band of interest.

4. The method of claim 1, wherein the selected two or more frequency sub-bands comprises a first frequency sub-band of the plurality of frequency sub-bands of the frequency band of interest and a second frequency sub-band of the plurality of frequency sub-bands of the frequency band of interest, and wherein the biomarker comprises a shift in a power distribution between the first frequency sub-band and the second frequency sub-band over time.

5. The method of claim 1, wherein the biomarker comprises a change in a peak frequency within the selected two or more frequency sub-bands of the frequency band of interest.

6. The method of claim 5:
wherein the frequency band of interest is the beta band,
wherein a first frequency sub-band of the selected two or more frequency sub-bands of the beta band includes higher frequencies relative to a second frequency sub-band of the selected two or more frequency sub-bands of the beta band,
wherein determining the bioelectrical brain signal includes the biomarker comprises detecting a shift in a peak amplitude of activity from the first frequency sub-band to the second frequency sub-band, and wherein the spectral characteristics of the two or more frequency sub-bands of the biomarker comprises the shift in the peak amplitude of activity from the first frequency sub-band to the second frequency sub-band.

7. The method of claim 1, wherein the biomarker comprises a predetermined characteristic of a distribution of a signal strength within the selected two or more frequency sub-bands of the frequency band of interest of the bioelectrical brain signal.

8. The method of claim 7, wherein the predetermined characteristic of the distribution comprises a bimodal peak.

9. The method of claim 7, wherein the predetermined characteristic of the distribution comprises one or more of a peak width less than or equal to a first threshold value, a peak width greater than or equal to a second threshold value, or a unimodal peak.

10. The method of claim 1, wherein the biomarker comprises a width or a variability of the two or more frequency sub-bands exhibiting a relatively high or low level of activity.

11. The method of claim 1, further comprising generating an indication in response to determining the bioelectrical brain signal includes the biomarker, wherein generating the indication comprises generating at least one of a visible message, an audible signal or a somatosensory notification.

12. The method of claim 11, further comprising storing the indication in the memory.

13. The method of claim 1, further comprising generating a patient diagnosis based on determining the bioelectrical brain signal includes the biomarker.

14. The method of claim 1, wherein controlling therapy delivery by the medical device to the patient comprises controlling the medical device to one of initiate or terminate therapy delivery to the patient.

15. The method of claim 1, wherein controlling therapy delivery by the medical device to the patient comprises modifying one or more therapy parameter values.

16. The method of claim 1, wherein receiving the bioelectrical brain signal comprises receiving, with the one or more processors, the bioelectrical brain signal sensed via one or more electrodes implanted within a brain of the patient.

17. The method of claim 1:
wherein the frequency band of interest is the beta band,
wherein a first frequency sub-band of the selected two or more frequency sub-bands of the beta band includes higher frequencies relative to a second frequency sub-band of the selected two or more frequency sub-bands of the beta band, and
wherein determining the bioelectrical brain signal includes the biomarker comprises determining whether a dominant amount of beta band activity is in the first frequency sub-band or the second frequency sub-band, and
wherein the spectral characteristics of a first biomarker of the plurality of biomarkers comprises the dominant amount of beta band activity in the first frequency sub-band, and the spectral characteristics of a second biomarker of the plurality of biomarkers comprises the dominant amount of beta band activity in the second frequency sub-band.

18. The method of claim 1, wherein the spectral characteristics include one or more of: a power level in one or more frequency sub-bands of the selected two or more frequency sub-bands or a spectral pattern, the spectral pattern including a pattern in a power distribution between frequency sub-bands of the selected two or more frequency sub-bands over time.

19. The method of claim 1, wherein the patient state comprises a patient-initiated state, including one or more of a movement state, a speech state, or a sleep state.

20. A system comprising:
a medical device configured to deliver therapy to a patient;
a sensing module configured to sense a bioelectrical brain signal of the patient;
a memory that stores biomarker information comprising a plurality of biomarkers, each biomarker of the plurality of biomarkers comprising spectral characteristics of two or more frequency sub-bands of a particular frequency band of a plurality of predetermined frequency bands; and
one or more processors configured to determine the bioelectrical brain signal includes a biomarker indicative of a patient state by at least:
selecting a frequency band of interest of the bioelectrical brain signal from the plurality of predetermined frequency bands based on the biomarker information,
wherein the predetermined frequency bands include two or more of a delta band, a theta band, an alpha band, a beta band, a gamma band, or a high gamma band, and
wherein the frequency band of interest includes a plurality of frequency sub-bands; and
after selecting the frequency band of interest, selecting two or more frequency sub-bands from the plurality of frequency sub-bands based on the biomarker information, wherein each of the selected two or more frequency sub-bands is narrower than the frequency band of interest, and
wherein the one or more processors are configured to control therapy delivery by the medical device to the patient based on determining the bioelectrical brain signal includes the biomarker.

21. The system of claim 20, wherein the one or more processors are configured to determine the bioelectrical brain signal includes the biomarker based on a spectral pattern of the bioelectrical brain signal in the selected two or more frequency sub-bands of the frequency band of interest.

22. The system of claim 20, wherein the selected two or more frequency sub-bands comprises a first frequency sub-band of the plurality of frequency sub-bands of the frequency band of interest and a second frequency sub-band of the plurality of frequency sub-bands of the frequency band of interest, and wherein the biomarker comprises a shift in a power distribution between the first frequency sub-band and the second frequency sub-band over time.

23. The system of claim 20, wherein the biomarker comprises a change in a peak frequency within the selected two or more frequency sub-bands of the frequency band of interest.

24. The system of claim 20, wherein the biomarker comprises a predetermined characteristic of a distribution of a signal strength within the selected two or more frequency sub-bands of the frequency band of interest of the bioelectrical brain signal.

25. The system of claim 24, wherein the predetermined characteristic of the distribution comprises one or more of a peak width less than or equal to a first threshold value, a peak width greater than or equal to a second threshold value, a unimodal peak, or a bimodal peak.

26. The system of claim 20, wherein the biomarker comprises a width or a variability of the two or more frequency sub-bands exhibiting a relatively high or low level of activity.

27. The system of claim 20, further comprising a user interface, wherein the one or more processors are configured to generate an indication in response to determining the bioelectrical brain signal includes the biomarker by at least controlling the user interface to generate at least one of a visible message, an audible signal or a somatosensory notification.

28. The system of claim 27, wherein the one or more processors are configured to store the indication in the memory.

29. The system of claim 20, further comprising a user interface wherein the one or more processors are configured to generate a patient diagnosis based on determining the bioelectrical brain signal includes the biomarker and present the patient diagnosis via the user interface.

30. The system of claim 20, wherein the one or more processors are configured to control therapy delivery by the medical device to the patient by at least modifying one or more therapy parameter values.

31. The system of claim 20, wherein at least two frequency sub-bands of the selected two or more frequency sub-bands do not overlap with each other.

32. The system of claim 20, wherein at least two frequency sub-bands of the selected two or more frequency sub-bands overlap with each other.

33. The system of claim 20, wherein the sensing module is configured to sense the bioelectrical brain signal via one or more electrodes configured to be implanted within a brain of the patient.

34. The system of claim 20:
wherein the frequency band of interest is the beta band,
wherein a first frequency sub-band of the selected two or more frequency sub-bands of the beta band includes higher frequencies relative to a second frequency sub-band of the selected two or more frequency sub-bands of the beta band, and
wherein the one or more processors are configured to determine the bioelectrical brain signal includes the biomarker by at least determining whether a dominant amount of beta band activity is in the first frequency sub-band or the second frequency sub-band, and
wherein the spectral characteristics of a first biomarker of the plurality of biomarkers comprises the dominant amount of beta band activity in the first frequency sub-band, and the spectral characteristics of a second biomarker of the plurality of biomarkers comprises the dominant amount of beta band activity in the second frequency sub-band.

35. The system of claim 20, wherein the spectral characteristics include one or more of: a power level in one or more frequency sub-bands of the selected two or more frequency sub-bands or a spectral pattern, the spectral pattern including a pattern in a power distribution between frequency sub-bands of the selected two or more frequency sub-bands over time.

36. The system of claim 20, wherein the patient state comprises a patient-initiated state, including one or more of a movement state, a speech state, or a sleep state.

37. A system comprising:
means for sensing a bioelectrical brain signal of a patient;
means for determining the bioelectrical brain signal includes a biomarker indicative of a patient state,
wherein the means for determining the bioelectrical brain signal includes the biomarker comprises:
means for selecting a frequency band of interest of the bioelectrical brain signal from a plurality of predetermined frequency bands based on biomarker information stored by a memory, wherein the biomarker information comprises a plurality of biomarkers, each biomarker of the plurality of biomarkers comprising spectral characteristics of two or more frequency sub-bands of a particular frequency band of the plurality of predetermined frequency bands,
wherein the predetermined frequency bands include two or more of a delta band, a theta band, an alpha band, a beta band, a gamma band, or a high gamma band, and
wherein the frequency band of interest includes a plurality of frequency sub-bands; and
means for selecting, after selecting the frequency band of interest, two or more frequency sub-bands from the plurality of frequency sub-bands based on the biomarker information,
wherein each of the selected two or more frequency sub-bands is narrower than the frequency band of interest; and
means for controlling therapy delivery by a medical device to the patient based on determining the bioelectrical brain signal includes the biomarker.

38. The system of claim 37, wherein the means for determining the bioelectrical brain signal includes the biomarker is configured to determine the bioelectrical brain signal includes the biomarker based on a spectral pattern of the bioelectrical brain signal in the selected two or more frequency sub-bands of the frequency band of interest.

39. The system of claim 37, further comprising means for generating an indication based on determining the bioelectrical brain signal includes the biomarker.

40. The system of claim 37:
wherein the frequency band of interest is the beta band,
wherein a first frequency sub-band of the selected two or more frequency sub-bands of the beta band includes higher frequencies relative to a second frequency sub-band of the selected two or more frequency sub-bands of the beta band,
wherein the means for determining the bioelectrical brain signal includes the biomarker determines the bioelectrical brain signal includes the biomarker by at least detecting a shift in a peak amplitude of activity from the first frequency sub-band to the second frequency sub-band,
wherein the spectral characteristics of the two or more frequency sub-bands of the biomarker comprises the shift in the peak amplitude of activity from the first frequency sub-band to the second frequency sub-band.

41. A non-transitory computer readable storage medium comprising instructions that, when executed by one or more processors, cause the one or more processors to:
receive a bioelectrical brain signal of a patient;
determine the bioelectrical brain signal includes a biomarker indicative of a patient state by at least:
selecting a frequency band of interest of the bioelectrical brain signal from a plurality of predetermined frequency bands based on biomarker information stored by a memory, wherein the biomarker information comprises a plurality of biomarkers, each biomarker of the plurality of biomarkers comprising spectral characteristics of two or more frequency sub-bands of a particular frequency band of the plurality of predetermined frequency bands,
wherein the predetermined frequency bands include two or more of a delta band, a theta band, an alpha band, a beta band, a gamma band, or a high gamma band, and
wherein the frequency band of interest includes a plurality of frequency sub-bands; and
after selecting the frequency band of interest, selecting two or more frequency sub-bands of the frequency band of interest from the plurality of frequency sub-bands based on the biomarker information,
wherein each of the selected two or more frequency sub-bands is narrower than the frequency band of interest; and
control therapy delivery by a medical device to the patient based on determining the bioelectrical brain signal includes the biomarker.

42. The non-transitory computer readable storage medium of claim 41, wherein the instructions, when executed by the one or more processors, cause the one or more processors to determine the bioelectrical brain signal includes the biomarker based on a spectral pattern of the bioelectrical brain signal in the selected two or more frequency sub-bands of the frequency band of interest.

* * * * *